United States Patent
Brownlie

(10) Patent No.: US 7,435,559 B2
(45) Date of Patent: Oct. 14, 2008

(54) METHODS AND COMPOSITIONS EMPLOYING A NOVEL STEAROYL-COA DESATURASE-HSCD5

(75) Inventor: Alison J. Brownlie, Vancouver (CA)

(73) Assignee: Xenon Pharmaceuticals Inc., Burnaby, B.C. (CA)

( * ) Notice: Subject to any disclaimer, the term of this patent is extended or adjusted under 35 U.S.C. 154(b) by 0 days.

(21) Appl. No.: 11/810,057

(22) Filed: Jun. 4, 2007

(65) Prior Publication Data

US 2007/0238648 A1    Oct. 11, 2007

Related U.S. Application Data

(62) Division of application No. 10/381,753, filed as application No. PCT/CA01/01354 on Sep. 26, 2001, now Pat. No. 7,232,662.

(60) Provisional application No. 60/235,640, filed on Sep. 26, 2000.

(51) Int. Cl.
*C12Q 1/26* (2006.01)
*C12N 9/02* (2006.01)

(52) U.S. Cl. .......................................... 435/25; 435/189
(58) Field of Classification Search ................. 435/4, 435/25, 189
See application file for complete search history.

(56) References Cited

U.S. PATENT DOCUMENTS 7,232,662 B2 *   6/2007   Brownlie ..................... 435/25

\* cited by examiner

*Primary Examiner*—Tekchand Saidha
(74) *Attorney, Agent, or Firm*—Elliot M. Olstein; Alan J. Grant

(57) ABSTRACT

A cDNA encoding a novel human stearoy-CoA desaturase (dubbed "hSCD5") as well as vectors and cells comprising such polynucleotide are disclosed. Also described are assay methods for determining the ability of small molecules and other chemical agents to increase or decrease he enzymatic activity and/or gene expression level of hSCD5 as well as processes for using such agents to treat, prevent or diagnose a variety of diseases and other conditions.

6 Claims, 8 Drawing Sheets

Figure 1

```
GAATTCGGCACGAGGTTCAGCCCGGGCAGCCATATGGGGGATACGCCAGCAACAGACGCCGGCCG
CCAAGATCTGCATCCCTAGGCCACGCTAAGACCCTGGGGAAGAGCGCAGGAGCCCGGGAGAAGG
GCTGGAAGGAGGGGACTGGACGTGCGGAGAATTCCCCCCTAAAAGGCAGAAGCCCCCGCCCCCAC
CCTCGAGCTCCGCTCGGGCAGAGCGCCTGCCTGCCTGCCGCTGCTGCGGGCGCCCACCTCGCCAG
CCATGCCAGGCCCGGCCACCGACGCGGGGAAGATCCCTTTCTGCGACGCCAAGGAAGAAATCCGT
GCCGGGCTCGAAAGCTCTGAGGGCGGCGGCGGCCCGGAGAGGCCAGGCGCGCGCGGGCAGCGGC
AGAACATCGTCTGGAGGAATGTCGTCCTGATGAGCTTGCTCCACTTGGGGGCCGTGTACTCCCTGG
TGCTCATCCCCAAAGCCAAGCCACTCACTCTGCTCTGGGCCTACTTCTGCTTCCTCCTGGCCGCTCT
GGGTGTGACAGCTGGTGCCCATCGCTTGTGGAGCCACAGGTCCTACCGGGCCAAGCTGCCTCTGAG
GATATTTCTGGCTGTCGCCAACTCCATGGCTTTCCAGAATGACATCTTCGAGTGGTCCAGGGACCA
CCGAGCCCACCACAAGTACTCAGAGACGGATGCTGACCCCCACAATGCCCGCCGGGGCTTCTTCTT
CTCCCATATTGGGTGGCTGTTTGTTCGCAAGCATCGAGATGTTATTGAGAAGGGGAGAAAGCTTGA
CGTCACTGACCTGCTTGCTGATCCTGTGGTCCGGATCCAGAGAAAGTACTATAAGATCTCCGTGGT
GCTCATGTGCTTTGTGGTCCCCACGCTGGTGCCCTGGTACATCTGGGGAGAGAGTCTGTGGAATTC
CTACTTCTTGGCCTCTATTCTCCGCTATACCATCTCACTCAACATCAGCTGGCTGGTCAACAGCGCC
GCCCACATGTATGGAAACCGGCCCTATGACAAGCACATCAGCCCTCGGCAGAACCCACTCGTCGC
TCTGGGTGCCATTGGTGAAGGCTTCCATAATTACCATCACACCTTTCCCTTTGACTACTCTGCGAGT
GAATTTGGCTTAAATTTTAACCCAACCACCTGGTTCATTGATTTCATGTGCTGGCTGGGGCTGGCCA
CTGACCGCAAACGGGCAACCAAGCCGATGATCGAGGCCCGGAAGGCCAGGACTGGAGACAGCAG
TGCTTGAACTTGGAACAGCCATCCCACATGTCTGCCGTTGCAACCTCGGTTCATGGCTTTGGTTAC
AATAGCTCTCTTGTACATTGGATCGTGGGAGGGGCAGAGGGTGGGGAAGGAACGAGTCAATGTG
GTTTGGGAATGTTTTTGTTTATCTCAAAATAATGTTGAAATACAATTATCAATGAAAAAACTTTCGT
TTTTTTTTTTGTTTGTTTTGTTTTTGAGACAGAGTCTCACTCTGTCACCCAGGCTGGAGTGCAGTGGC
GCAGTCTCGGCTCACTGCAGCCTCCACCTACCTGGTTCAAGCAATTCTCCTGCCTCAGCCTCCTGAG
TAGCTGAGATTACAGGAGCCTGCCACCACACCCAGCTAATTTTTTGTATTTTTAGTAGAGACAGG
GTTTCATCATGTTGGCCAGACTGGCCTCGAATTCCTGACCTCAGGCAATCCACCCGCCTCGGCCTC
CCAAAGAGCTGGGATTACAGGCGTGAGCCACCGCACCCTGCCGAAAAAAACTTTTTTTTTTTTGAG
ACGGAGGCTCGCTCTGTCCCCCAGGCTGGAGTGCAGTGGCGAGATCTCAGCTCACTGCAAGCTCCG
CCTCCCGGGTTCACGCCATTCTCCTGCCTCAGCCTCCCGAGTAGCTGGGAGCCAGCGCGCCCAGCC
TAAAAAACTTTTCAAGTCAATATTACTACGATTTAACATTAGAGTGTGGACATGTGATTTAATCGC
TATAGCTAAAATACGTCAAATATACGTTGTCATGTGCTTGAACATGATGCTAACCCTGACAGGATG
AAGGAAAGTAATATTCTTTCAGTGTAGTTCAGGAGAGCATTTGTTTTCTTTTCTACCAATTAACCCA
TCATTGCTTTTAAACAACCATCTGAAGGAGCAGAGAGGCAGGGTAGAAGACAGAAGGGGGATCTA
TGTGGTAACTAAAGAATGTTTCTGTTTTGTTAATTATTGTGTGTGTGTGGTTTTATTGTTTGCTTAAG
AGAATCAAAAACTGAAAAAAATGAGAATACAGGAAATGGCTCTTGTTTATTTTTTTGCTGTGTTTA
CAGCTTGTTAATGCTCTACTGTCTTTGTTTCAAGAGAGATTTGTTCACTGCCCAGCTCGTTTTGTGT
CCTGAGCCCTATGGCCAGCCCACCTTATAAATCATGCCTGTTTAGATGTTTGATTTTGTTCTGTTTG
CTATTGTTATCTTAAAGGTGTATAACTCTGACATGCCAGACATCAAATTAAGCTCAAATTAAGCTC
TCGTTTAAATGTTTAAGCACCTAATTTATATTCTAATTGATCCCAGCCACTGATGCATGTACTTTAG
CTACTTCTGCTAAATAAGCATATTAATTTTCCACATCAGACCATCAGATCTTGAGAACCAACAGTT
ATCTAGAATTCCGTGTCTACTAATGTTTCACCTGCATGCAGCCTTCATTAATTTTGTAGCAAAATAT
AAAGTGATCATTATGTAGCTTCTGGATTAAAAAAATTTGTGTGTGAAGTTGCTTTGTAAAGTGCAT
GTGGAATTAATGGGACAGTGTGCCCTTTGTGTTAGATGTTAGAGCAAAAGAAAGGGCTTATAGTGT
TAGTATTGGAGCACTTTGAAGATAGATATTTTCAGAAAAGATGTAGGATTTAAAAGTTAAATTTTA
AATTTTAGAAAAAGATATGATGGCAATTGGAAATAGTCACAATGAAGTTCTTCATCCAGTAGGTGT
TTAACAGTGTTATTTTGCCACTGGTAATGTGTAAACTGTGAGTGATTTACAATAAATGATTATGAA
TTC
```

Figure 2

MPGPATDAGKIPFCDAKEEIRAGLESSEGGGGPERPGARGQRQNIVWRNVVLMSLLH
LGAVYSLVLIPKAKPLTLLWAYFCFLLAALGVTAGAHRLWSHRSYRAKLPLRIFLAV
ANSMAFQNDIFEWSRDHRAHHKYSETDADPHNARRGFFFSHIGWLFVRKHRDVIEK
GRKLDVTDLLADPVVRIQRKYYKISVVLMCFVVPTLVPWYIWGESLWNSYFLASILR
YTISLNISWLVNSAAHMYGNRPYDKHISPRQNPLVALGAIGEGFHNYHHTFPFDYSA
SEFGLNFNPTTWFIDFMCWLGLATDRKRATKPMIEARKARTGDSSA

Figure 3A

```
mSCD1       1  -MPAHMLQEISSSYTTTTTITAPPSGNER---EKVKTVPLHLEEDIRPEMKEDIHDPTYQ
mSCD2       1  -MPAHILQEISGAYSATTTITAPPSGGQQNGGEKFEKSSHHWGADVRPELKDDLYDPTYQ
hSCD1       1  MPAHLLQDDISSSYTTTTITAPPSRVLQNGGDKLETMPLYLEDDIRPDIKDDIYDPTYK
CarpSCD1    1  ---------------------------------MPDREIKSPIWHPEPGTVEDVFDHTYK
CarpSCD2    1  ---------------------------------MPDRDIKSPIWHP--ETVEDVFDHTYK
chicken     1  --MPAHLLQEEEFSSASSTTTVTSRVTKNGNVIMEKDLLNHDDVAAERGMVDDLFDETYR
SCD5        1  -----------------------MPGPATDAGKIPFCDAKEEIRAGLESSEGGGGPE
Dros        1  -MPPNAQAGAQSISDSLIAAASAAADAGQSPTKLQEDSTGVLFECDVETTDGGLVKDITV
C.elegans   1  ----------------------MTVKTRSNIAKKIEKDGGPETQYLAVDPNEIIQLQE mSCD1      57  DEEGPPPKLEYVWRNIILMVLLHLGGLYGIILVPS-CKLYTALFGIFYYMTSALGITAGA
mSCD2      60  DDEGPPPKLEYVWRNIILMALLHLGALYGITLVPS-CKLYTCLFAYLYYVISALGITAGA
hSCD1      61  DKEGPSPKVEYVWRNIILMSLLHLGALYGITLIPT-CKFYTWLWGVFYYFVSALGITAGA
CarpSCD1   28  EKEGPKPPTVIVWRNVILMSLLHLGALYGLFLFPS-ARALTWIWFFGCLLFSALGITAGA
CarpSCD2   26  EKEGPKPPTVIVWRNVLLMAFLHTGALYGLVLFPS-ASVLTWIWFLACFVFSALGVTAGA
chicken    59  EKEGPKPPLRYVWRNIILMSLLHLGAIIGLTLIPS-AKIQTLAWAILCFVLSALGITAGS
SCD5       35  RPGARGQRQNIVWRNVVLMSLLHLGAVYSLVLIPK-AKPLTLLWAYFCFLLAALGVTAGA
Dros       60  MKKAEKRLLKLVWRNIIAFGYLHLAALYGAYLMVTSAKWQTCILAYFLYVISGLGITAGA
C.elegans  37  ESKKIPYKMEIVWRNVALFAALHFAAAIGLYQLIFEAKWQTVIFTFLLYVFGGFGITAGA mSCD1     116  HRLWSHRTYKARLPLRIFLIIANTMAFQNDVYDWARDHRAHHKFSETHADPHNSRRGFFF
mSCD2     119  HRLWSHRTYKARLPLRLFLIIANTMAFQNDVYEWARDHRAHHKFSETHADPHNSRRGFFF
hSCD1     120  HRLWSHRSYKARLPLRLFLIIANTMAFQNDVYEWARDHRAHHKFSETHADPHNSRRGFFF
CarpSCD1   87  HRLWSHRSYKASLPLQIFLALGNSMAFQNDIYEWSRDHRVHHKYSETDADPHNAVRGFFF
CarpSCD2   85  HRLWSRRSYKASLPLRIFLAFANSMGFQNDIYEWSRDHRVHHKYSETDADPHNAVRGFFF
chicken   118  HRLWSHRSYKATLPLRIFLTIANSMAFQNDIYEWARDHRVHHKFSETHADPHNAMRGYFF
SCD5       94  HRLWSHRSYRAKLPLRIFLAVANSMAFQNDIFEWSRDHRAHHKYSETDADPHNARRGFFF
Dros      120  HRLWAHRSYKAKWPLRVILVIFNTIAFQDAAYHWARDHRVHHKYSETDADPHNATRGFFF
C.elegans  97  HRLWSHKSYKATTPMRIFLMILNNIALQNDVIEWARDHRCHHKWTDTDADPHNTTRGFFF mSCD1     176  SHVGWLLVRKHPAVKEKGGKLDMSDLKAEKLVMFQRRYYKPGLLLMCFILPTLVPWYCWG
mSCD2     179  SHVGWLLVRKHPAVKEKGGKLDMSDLKAEKLVMFQRRYYKPDLLLMCFVLPTLVPWYCWG
hSCD1     180  SHVGWLLVRKHPAVKEKGSTLDLSDLEAEKLVMFQRRYYKPGLLLMCFILPTLVPWYFWG
CarpSCD1  147  SHVGWLLVRKHPDVIEKGRKLELSDLKADKVVMFQRRFYKPSVLLMCFFVPTFVPWYVWG
CarpSCD2  145  SHIGWLLVRKHPDVIEKGRKLELSDLKADKVVMFQRRFYKSSVLLMCFFVPTFVPWYVWG
chicken   178  SHMAWLLVRKHPDVIEKGQKLDLSDLKADKVVMFQRRYYKPSVVLLCFTLPTLVPWYFWD
SCD5      154  SHIGWLFVRKHRDVIEKGRKLDVTDLLADPVVRIQRKYYKISVVLMCFVVPTLVPWYIWG
Dros      180  SHVGWLLCKKHPEVKAKGKGVDLSDLRADPILMFQKKYYMILMPIACFIIPTVVPMYAWG
C.elegans 157  AHMGWLLVRKHPQVKEQGAKLDMSDLLSDPVLVFQRKHYFPLVILCCFILPTIIPVYFWK mSCD1     236  ETFVNSLFVSTFLRYTLVLNATWLVNSAAHLYGYRPYDKNIQSRENILVSLGAVGEGFHN
mSCD2     239  ETFVNSLCVSTFLRYAVVLNATWLVNSAAHLYGYRPYDKNISSRENILVSMGAVGERFHN
hSCD1     240  ETFQNSVFVATFLRYAVVLNATWLVNSAAHLFGYRPYDKNISPRENILVSLGAVGEGFHN
CarpSCD1  207  ESLWVAYFVPALLRYALVLNATWLVNSAAHMWGNRPYDSSINPRENRFVTFSAIGEGFHN
CarpSCD2  205  ESLWVAYFVPAVLRYALVLNATWLVNSAAHMWGNRPYDSSINPRENRFVAFSAIGEGFHN
chicken   238  ESIIISFFIPAILRYTLGLNATWLVNSAAHMFGNRPYDQNINPRENPLVSVGALGEGFHN
SCD5      214  ESLWNSYFLASILRYTISLNISWLVNSAAHMYGNRPYDKHISPRQNPLVALGAIGEGFHN
Dros      240  ESFMNAWFVATMFRWCFILNVTWLVNSAAHKFGGRPYDKFINPSENISVAILAFGEGWHN
C.elegans 217  ETAFIAFYTAGTFRYCFTLHATWCINSAAHYFGWKPYDSSITPVENVFTTIAAVGEGGHN
```

Figure 3B

```
mSCD1       296  YHHTFPFDYSASEYRWHINFT-TFFIDCMAALGLAYDRKKVSKATVLARIKRTGDGSHKS
mSCD2       299  YHHAFPYDYSASEYRWHINFT-TFFIDCMALLGLAYDRKRVSRAAVLARIKRTGDGSCKS
hSCD1       300  YHHSFPYDYSASEYRWHINFT-TFFIDCMAALGLAYDRKKVSKAAILARIKRTGDGNYKS
CarpSCD1    267  YHHTFPFDYATSEFGCKLNLTTCCFIDLMCFLGLAREPKRVSREAVLARAQRTGDGSHWS
CarpSCD2    265  YHHTFPFDYATSEFGCKLNLT-TCFIDLMCFLGLAREPKRVSREAALARAQRTGDGSHRT
chicken     298  YHHTFPYDYSTSEFGWRFNLT-TAFIDLMCLLGLASDRKKVSKEVILARKMRTGDGSHKS
SCD5        274  YHHTFPFDYSASEFGLNFNPT-TWFIDFMCWLGLATDRKRATKPMIEARKARTGDSSA--
Dros        300  YHHVFPWDYKTAEFGKYSLNFTTAFIDFFAKIGWAYDLKTVSTDIIKKRVKRTGDGTHAT
C.elegans   277  FHHTFPQDYRTSEYSLKYNWT-RVLIDTAAALGLVYDRKTACDEIIGRQVSNHGCDIQRG mSCD1       355  S---------------------
mSCD2       358  G---------------------
hSCD1       359  G---------------------
CarpSCD1    327  G---------------------
CarpSCD2    324  G---------------------
chicken     357  G---------------------
SCD5             ----------------------
Dros        360  WGWGDVDQPKEEIEDAVITHKKSE
C.elegans   336  KSIM------------------
```

Figure 4A

```
mSCD1   1   -MPAHMLQEISSSYTTTTTITAPPSG---NEREKVKTVPLHLEEDIRPEMKEDIHDPTYQDEEGPPPKLEYVWRNIILMV
mSCD3   1   -MPAHMLQEISSSYTTTTTITAPPSG---NEREKVKTVPLHLEEDIRPEMKEDIHDPTYQDEEGPPPKLEYVWANIILMV
mSCD4   1   MPGHLLQEEMTPSYTTTTITAPPSGSLQNGREKVKTVPLYLEEDIRPEMKEDIYDPTYQDEEGPPPKLEYVWANIILMA
mSCD2   1   -MPAHILQEISGAYSATTTITAPPSGGQQNGEKFEKSSHHWGADVRPELKDDLYDPTYQDDEGPPPKLEYVWRNIILMA
hSCD1   1   MPAHLLQDDISSSYTTTTTITAPPSRVLQNGGDKLETMPLYLEDDIRPDIKDDIYDPTYKDKEGPSPKVEYVWRNIILMS
hSCD5   1   MPGPATDAG--------------------KIP-FCDAKEEIRAGLESSEGGGPERPGARGQRQNIVWRNVVLMS mSCD1   77   LLHLGGLYGIILVPSCKLYTALFGIFYYMTSALGITAGAHRLWSHRTYKARLPLRIFLIIANTMAFQNDVYDWARDHRAH
mSCD3   77   LLHLGGLYGIILVPSCKLYTCLFGIFYYMTSALGITAGAHRLWSHRTYKARLPLRIFLIIANTMAFQNDVYEWARDHRAH
mSCD4   81   LLHVGALYGITLVPSCKLYTLFEAFVYYVISIEGIGAGVHRLWSHRTYKARLPLRIFLIIANTMAFQNDVYEWARDHRAH
mSCD2   80   LLHLGALYGITLVPSCKLYTCLFAYLYYVISALGITAGAHRLWSHRTYKARLPLRLFLIIANTMAFQNDVYEWARDHRAH
hSCD1   81   LLHLGALYGITLIPTCKFYTWLWGVFYFVSALGITAGAHRLWSHRSYKARLPLRLFLIIANTMAFQNDVYEWARDHRAH
hSCD5   55   LLHLGAVYSLVLIPKAKPLTLLWAYFCFLLAALGVTAGAHRLWSHRSYRAKLPLRIFLAVANSMAFQNDIFEWSRDHRAH mSCD1   157  HKFSETHADPHNSRRGFFFSHVGWLLLVRKHPAVKEKGGKLDMSDLKAEKLVMFQRRYYKPGLLLMCFILPTLVPWYCWGE
mSCD3   157  HKFSETHADPHNSRRGFFFSHVGWLLLVRKHPAVKEKGGKLDMSDLKAEKLVMFQRRYYKPGLLLMCFILPTLVPWYCWGE
mSCD4   161  HKFSETHADPHNSRRGFFFSHVGWLLVAKHPAVKEKGGKLDMSDLKAEKLVMFQRRYYKPGILLMCFILPTLV-WYCWGE
mSCD2   160  HKFSETHADPHNSRRGFEFSHVGWLLLVRKHPAVKEKGGKLDMSDLKAEKLVMFQRRYYKPDLLLMCFVLPTLVPWYCWGE
hSCD1   161  HKFSETHADPHNSRRGFFFSHVGWLLLVRKHPAVKEKGSTLDLSDLEAEKLVMFQRRYYKPGLLLMCFILPTLVPWYFWGE
hSCD5   135  HKYSETDADPHNARRGFFFSHIGWLFVRKHRDVIEKGRKLDVTDLLADPVVRIQRKYYKISVVLMCFVVPTLVPWYIWGE
```

Figure 4B

```
mSCD1  237  TFVNSLFVSTFLRYTLVLNATWLVNSAAHLYGYRPYDKNIQSRENILVSLGAVGEGEFHNYHHTFPEDYSASEYRWHINFT------
mSCD3  237  TFVNSLFVSTFLRYTLVLNATWLVNSAAHLYGYRPYDK-IQSRENILVSLGAV------------------------------------
mSCD4  240  TFLNSFYVATLLRYAVVLNATWLVNSAAHLYGYRPYDKNIDPRQNALVSLGSMGEGEFHNYHHAFPYDSASEYRWHINFT---------
mSCD2  240  TFVNSLCVSTFLRYAVVLNATWLVNSAAHLYGYRPYDKNISSRENILVSMGAVGERFHNYHHAFPYDSASEYRWHINFT----------
hSCD1  241  TFQNSVFVATFLRYAVVLNATWLVNSAAHLFGYRPYDKNISPRENILVSLGAVGEGEFHNYHHSFPYDSASEYRWHINFT---------
hSCD5  215  SLWNSYFLASILRYTISLNISWLVNSAAHMYGNRPYDKHISPRQNPLVALGAIGEGEFHNYHHTFPEDYSASEFGLNFNPT mSCD1  317  TFFIDCMAALGLAYDRKKVSKATVLARIKRTGDGSHKSS
mSCD3  n.SCD3
mSCD4  320  TFFIDCMAALGLAYDRKRVSKATVLARIKRTGDGSHKSG
mSCD2  320  TFFIDCMALLGLAYDRKRVSRAAVLARIKRTGDGSCKSG
hSCD1  321  TFFIDCMAALGLAYDRKKVSKAAILARIKRTGDGNYKSG
hSCD5  295  TWFIDEMCWLGLATDRKRATKPMIEARKARTGDSSA---
```

METHODS AND COMPOSITIONS EMPLOYING A NOVEL STEAROYL-COA DESATURASE-HSCD5

This application is a division of divisional of U.S. Ser. No. 10/381,753, filed 2 Oct. 2003, now U.S. Pat. No. 7,232,662, which was a national phase application of PCT/CA01/01354, filed 26 Sep. 2001, which claimed priority of U.S. Provisional Application 60/235,640, filed 26 Sep. 2000, the disclosures of which are hereby incorporated by reference in their entirety.

FIELD OF THE INVENTION

The present invention relates generally to the field of human stearoyl-CoA desaturase enzymes and the effects of modulation of such enzymes with various disease processes, including the use of such enzymes, and the genes encoding them, in the development of therapeutic screening processes.

BACKGROUND OF THE INVENTION

Acyl desaturase enzymes catalyze the formation of double bonds in fatty acids derived from either dietary sources or de novo synthesis in the liver. Mammals synthesize four desaturases of differing chain length specificity that catalyze the addition of double bonds at the Δ9, Δ6, Δ5 and Δ4 positions. Stearoyl-CoA desaturases (SCDs) introduce a double bond in the Δ9-position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesterol esters, and also function in gene transcription, and as precursors for other biologically active compounds such as thromboxanes and prostaglandins.

A number of mammalian SCD genes have been cloned. For example, two genes have been cloned from rat (SCD1, 2)[1,2] and four SCD genes have been isolated from mouse (SCD1, 2, 3, 4.)[3,4] Until now, a single SCD gene, SCD1, has been characterized in humans.[5]

Alterations in SCD gene expression and/or enzyme activity have been correlated with disease states. These disease states may fall into two classes: those that are direct effects of decreased SCD enzyme activity and those that have been correlated with changes in SCD activity where the causal relationship between enzyme activity and the disease state is not known.

Mutations in mouse SCD1 cause disturbances in skin lipids, abnormal differentiation of sebaceous glands and go on to develop an alopecia similar to clinical scarring alopecias seen in humans[6]. In addition, mutants homozygous for a disruption of SCD1 show corneal defects, suggesting that SCD1 is required for ocular barrier function in the eye[7]. These animals also show striking lipid abnormalities, including decreased levels of liver cholesterol esters and triglycerides, and reportedly increased plasma HDL levels[8].

Approximately half of all human patients with coronary-artery disease have a low concentration of high density lipoprotein-cholesterol (HDL-C)[24]. Clustering studies have shown that high triglycerides, low HDL-C, diabetes, hypertension and hyperuricemia were related to insulin resistance/high insulin levels and central and/or obesity[25]. Thus, the inventor hereto has recognized that modulation of SCD activity in humans may have an effect on lipid metabolism, and play a role in propensity to develop atherosclerosis and cardiovascular disease.

In accordance with the present invention, there is disclosed herein sequence and gene expression data confirming the existence of an additional SCD gene in humans (hSCD5).

BRIEF SUMMARY OF THE INVENTION

In one aspect, the present invention relates to isolated polynucleotides comprising polynucleotide sequences having at least 60% identical, preferably at least 80% identical, most preferably at least 90% identical, especially at least 95% identical, and most especially sequences identical, to the sequence of SEQ ID NO: 1 or the complement thereof. Such polynucleotide sequences may be genomic or non-genomic, with the latter including DNA, RNA, cDNA or any type of wholly synthetic sequence prepared by cloning or direct chemical synthesis thereof and include complements of any of these.

In another aspect, the present invention relates to isolated polynucleotides comprising a polynucleotide sequence encoding the same polypeptide as the polynucleotide with the sequence of SEQ ID NO: 1. Such polynucleotide sequences may be genomic or non-genomic, with the latter including DNA, RNA, cDNA or any type of wholly synthetic sequence prepared by cloning or direct chemical synthesis thereof. The complements of all polynucleotides disclosed herein are also specifically contemplated. Such polypeptide will commonly have desaturase activity.

An additional aspect of the present invention relates to an isolated stearoyl-CoA desaturase (hSCD5-SEQ ID NO: 2) encoded by the isolated polynucleotides disclosed according to the invention, to vectors comprising such polynucleotides and to recombinant eukaryotic cells, and cell lines, preferably mammalian cells, and cell lines, and most preferably human cells, and cell lines, transfected so as to comprise such vectors and/or said polynucleotides and wherein said cells express hSCD5.

Using the polynucleotides, enzymes, and cells disclosed herein, it is an object of the present invention to provide a process for determining the ability of an agent to modulate the activity of said human stearoyl-CoA desaturase (hSCD5).

It is also an object of the present invention to provide agents capable of modulating the activity and/or expression of human stearoyl-CoA desaturase 5 (hSCD5) as disclosed herein, especially where said modulating ability was first determined using an assay comprising hSCD5 or a gene encoding hSCD5. Compositions comprising such agents are specifically contemplated.

It is another object of the present invention to provide screening processes, including high throughput screening processes, for determining the efficacy of potential therapeutic and diagnostic drugs for treating the diseases described herein, preferably diseases in which increased or decreased activity or expression of stearoyl-CoA desaturase (hSCD5 of the invention) plays a key role in mediating such disease.

It is a still further object of the present invention to provide agents wherein said agent is useful in treating, preventing and/or diagnosing a disease or condition.

It is a yet further object of the present invention to provide a process for preventing or treating a disease or condition in a patient afflicted therewith comprising administering to said patient a therapeutically or prophylactically effective amount of a composition as disclosed herein.

In other aspects, the present invention also provides a process for diagnosing a disease or condition in a patient, commonly a human being, suspected of being afflicted therewith, or at risk of becoming afflicted therewith, comprising obtaining a tissue sample from said patient and determining the level of activity of hSCD5 in the cells of said tissue sample and comparing said activity to that of an equal amount of the corresponding tissue from a patient not suspected of being afflicted with, or at risk of becoming afflicted with, said disease or condition.

BRIEF DESCRIPTION OF THE DRAWINGS

FIG. 1 shows the nucleotide sequence of a cDNA encoding the novel human stearoyl-CoA desaturase enzyme (hSCD5) of the present invention (the sequence of SEQ ID NO: 1). The sequence is 3042 nucleotides in length and shows start and stop codons in bold and with northern blot underlined.

FIG. 2 shows a putative amino acid sequence (SEQ ID NO: 2) derived from the cDNA sequence of FIG. 1.

FIG. 3 shows a cross species comparison of amino acid sequences for the species shown in Table 1. FIGS. 3A and 3B follow in sequence. The compared sequences are as follows: mouse mHCD1 (SEQ ID NO: 3), mHCD2 (SEQ ID NO: 4), human hSCD1 (SEQ ID NO: 5), carp SCD1 (SEQ ID NO: 6), carp SCD2 (SEQ ID NO: 7), chicken (SEQ ID NO: 8), *Drosophila melanogaster* (SEQ ID NO: 9) and *Caenorhabditis elegans* (SEQ ID NO: 10).

FIG. 4 shows a comparison of amino acid sequences of human and mouse SCD family members with conserved catalytic domains in bold. FIGS. 4A and 4B follow in sequence. Additional sequences are mouse mSCD3 (SEQ ID NO: 11) and mSCD4 (SEQ ID NO: 12).

DETAILED SUMMARY OF THE INVENTION

Figure 5:
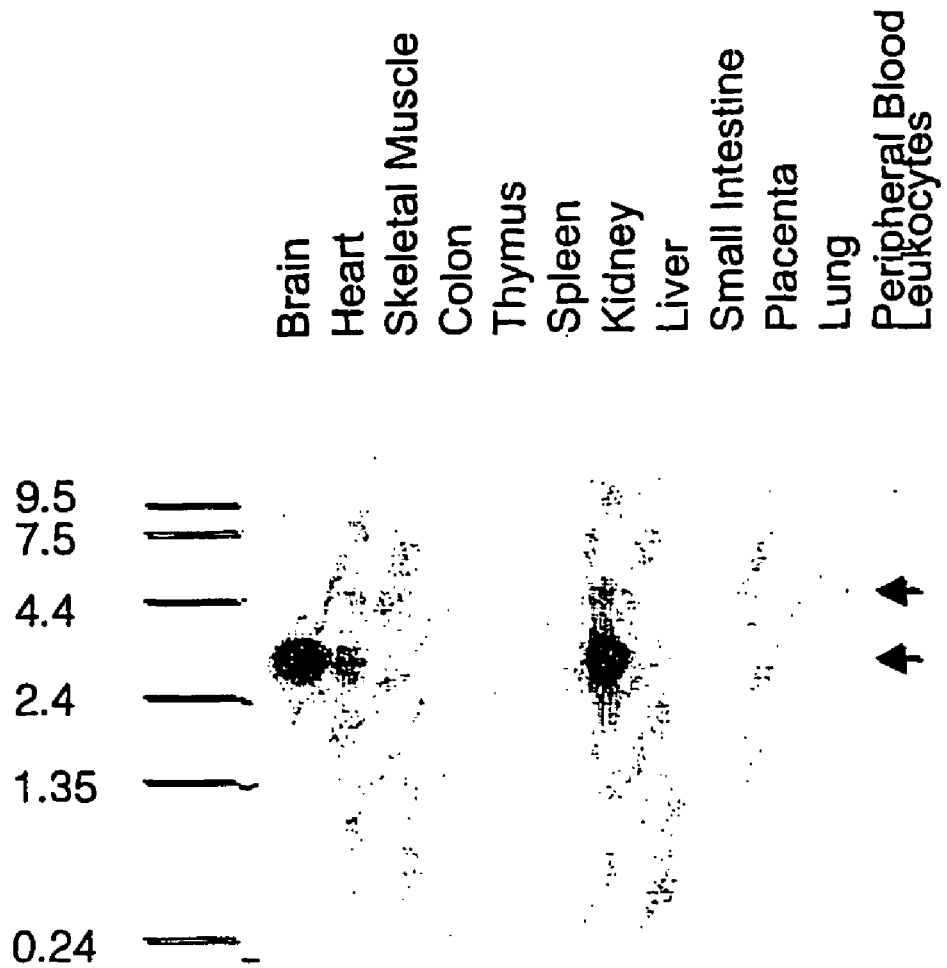
FIG. 5 shows a northern blot showing the presence or absence of hSCD5 mRNA transcripts in a variety of human tissues.

The present invention relates to human stearoyl-CoA desaturase enzymes and uses thereof relying on the effects of modulation of such enzymes with various disease processes, including the use of such enzymes, and the genes encoding them, in the development of therapeutic screening processes.

In one aspect the present invention relates to an isolated polynucleotide comprising a non-genomic polynucleotide having at least 90% identity, preferably 95% identity, most preferably at least a 98% identity to the sequence of SEQ ID NO: 1, especially where said sequences are the same and including any of the complements of any of the foregoing.

In accordance with the present invention, the term "percent identity" or "percent identical, " when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100[1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

The present invention further relates to an isolated polynucleotide comprising a non-genomic polynucleotide encoding the same polypeptide as the polynucleotide with the sequence of SEQ ID NO: 1 and represented by the reading frame starting with the initiating (ATG) codon represented in boldface in FIG. 1: In specific embodiments thereof this non-genomic polynucleotide is a DNA, preferably a cDNA and complements thereof.

In accordance with the present invention, there is disclosed herein the nucleotide sequence of a non-genomic DNA, here a cDNA, encoding a novel hSCD5. Bacterial artificial chromosomes (BAC's) containing the full length human genomic sequence of hSCD5 have also been isolated. The cDNA sequence bears a 56% sequence homology with the known human sequence the known human gene coding for Stearoyl-CoA Desaturase (hSCD1). In addition, the sequence disclosed according to the invention herein maps to chromosome location 4q21 (hSCD1 maps to chromosome 10) and exhibits a high degree of divergence at the 5'-end. Heretofore, the full length sequence has not been available in the public domain.

Further to the disclosure herein at least three overlapping BACs containing the human genomic sequence have been identified that are commercially available (Research Genetics Inc., Huntsville, Ala.) as (comment: BAC RP11 141F19 might be chimeric and is no longer being studied), RP11 -791G16 (GenBank Accession No. AC067942), and RP11-57B24 (GenBank Accession No. AC073413). And additional BAC, not found in GenBank, named RP11-683C18 has also been identified using a BAC fingerprint map. 791G16 contains only 3'UTR and exon 6 of SCD5. C18683 contains 3'UTR, as well as exons 3, 4, 5, 6. 57B24 contains at least 3'UTR, as well as exons 2, 3, 4, 5. 57B24 extends further 5', and therefore may contain exon 1 and 5'UTR as well. This BAC is being further analyzed to see if it encodes the entire SCD5 gene. Further, review of the publicly available morbidity map fails to indicate any disease linked to the chromosomal position of hSCD5 as disclosed herein. Sequence homology with related polypeptides was found to be as follows for the full length sequences:

TABLE 1

Cross-Species Sequence Homologies

| Gene Sequence | hSCD1 | hSCD5 |
|---|---|---|
| hSCD1 | — | 57% |
| hSCD5 | 57% | — |
| Chicken SCD | 66% | 61% |
| Carp SCD2 | 60% | 61% |
| CarpSCD1 | 62% | 60% |
| mSCD1 | 85% | 56% |
| mSCD2 | 82% | 56% |

TABLE 1-continued

Cross-Species Sequence Homologies

| Gene Sequence | hSCD1 | hSCD5 |
|---|---|---|
| Drosophila SCD | 48% | 45% |
| C. elegans | 45% | 41% |

By analogy, mutations in hSCD1 have been identified as the basis for the Asebia mouse phenotype which, inter alia, have no hair (due to a defect in their sebaceous glands) and have decreased levels of TG (triglycerides) and VLDL (very low density lipoproteins). No consistent elevation of HDL was observed in these animals; however, this may be due to the fact that mice lack the enzyme CETP (cholesterol ester transfer protein). In mammals with CETP activity, decreased VLDL causes a resultant increase in HDL, since CETP functions to transfer cholesterol from HDL to VLDL. In the absence of substrate, that is VLDL, it would be expected that CETP positive mammals would show increased levels of HDL. Elevated HDL levels provide considerable cardiovascular protection.

Thus, modulators of hSCD5 are expected to effectively treat cholesterol disorders, lipidemias, cardiovascular disease, atherosclerosis, diabetes, obesity, kidney dysfunction, and related disorders. In particular such modulators are expected to be useful in increasing HDL levels in a patient and/or for reducing triglyceride levels in a patient. Human subjects having increased HDL levels and/or decreased triglyceride levels have a highly significant correlation with reduced cardiovascular disease and reduced coronary artery disease[24,25]. Such modulators may also be effective in treating baldness (see, for example, WO 00/09754) and various skin diseases, as well as such diverse maladies as cancer and multiple sclerosis.

A search of the patent databases reveals that numerous ESTs (expressed sequence tags) are available for this gene but none has identified it specifically as an hSCD gene for a desaturase. The EST database profile indicates organs that might be affected by modulators of hSCD5 as including muscle, colon, adrenal, aorta, prostate, stomach, kidney, ovary, germ cell, lung, foreskin, brain, eye, parathyroid gland, ear, breast, uterus, placenta, and testis, all of which may be either adult or embryonic tissues. There is a Unigene entry NM_024906 (Mar. 18, 2001) that describes this gene with only a partial amino acid sequence and makes no mention of any desaturase activity.

As used herein and except as noted otherwise, all terms are defined as given below.

In accordance with the present invention, the term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by internal nontranslated sequences, or introns, which are typically present in eukaryotic genes. Sequences of nontranslated DNA may be present downstream from the open reading frame, where the same do not interfere with manipulation or expression of the coding regions.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

"Isolated" in the context of the present invention with respect to polypeptides or polynucleotides means that the material is removed from its original environment (e.g., the natural environment if it is naturally occurring). For example, a naturally occurring polynucleotide or polypeptide present in a living organism is not isolated, but the same polynucleotide or polypeptide, separated from some or all of the co-existing materials in the natural system, is isolated. Such polynucleotides could be part of a vector and/or such polynucleotides or polypeptides could be part of a composition, and still be isolated in that such vector or composition is not part of its natural environment The polypeptides and polynucleotides of the present invention are preferably provided in an isolated form, and preferably are purified to homogeneity.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, claimed polypeptide which has a purity of preferably 0.001%, or at least 0.01% or 0.1%; and even desirably 1% by weight or greater is expressly contemplated.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means that polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region whose expression product retains essentially the same biological function or activity as the expression product of the complete coding region.

The term "primer" means a short nucleic acid sequence that is paired with one strand of DNA and provides a free 3'OH end at which a DNA. polymerase starts synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein (and wherein any one of these is a "reading frame").

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

The present invention further relates to a polypeptide which has the deduced amino acid sequence of SEQ ID NO: 2, as well as fragments, analogs and derivatives of such polypeptide that exhibit hSCD activity.

The terms "fragment," "derivative" "and analog" when referring to the polypeptide, means a polypeptide which retains essentially the same biological function or activity as such polypeptide. Thus, an analog includes a proprotein which can be activated by cleavage of the proprotein portion to produce an active mature polypeptide. Such fragments, derivatives and analogs must have sufficient similarity to the polypeptide of SEQ ID NO:2 so that activity of the native polypeptide is retained.

The polypeptide of the present invention may be a recombinant polypeptide, a natural polypeptide or a synthetic polypeptide, preferably a recombinant polypeptide.

The fragment, derivative or analog of the polypeptide (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

As known in the art "similarity" between two polypeptides is determined by comparing the amino acid sequence and its conserved amino acid substitutes of one polypeptide to the sequence of a second polypeptide.

In accordance with the foregoing, the present invention also relates to an isolated stearoyl-CoA desaturase encoded by the isolated polynucleotide of the invention.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, such terms refer to the products produced by treatment of said polynucleotides with any of the common endonucleases.

The present invention also relates to vectors which contain polynucleotides of the present invention, host cells which are genetically engineered with vectors of the invention, especially where such cells result in a cell line that can be used for assay of hSCD, especially hSCD5, activity and production of polypeptides of the invention by recombinant techniques.

Host cells, preferably insect cells of Spodoptera species, most especially SF9 cells, are genetically engineered (transduced or transformed or transfected) with the vectors, especially baculovirus) of this invention which may be, for example, a cloning vector or an expression vector. Such vectors can include plasmids, viruses and the like. The engineered host cells are cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein. Such transformation will be permanent and thus give rise to a cell line that can be used for further testing. Such cell lines used for testing will commonly be mammalian cells, especially human cells.

As representative examples of appropriate hosts, there may be mentioned *Spodoptera* Sf9 (and other insect expression systems) and animal cells such as CHO, COS or Bowes melanoma; adenoviruses; plant cells, and even bacterial cells, etc, all of which are capable of expressing the polynucleotides disclosed herein. The selection of an appropriate host is deemed to be within the knowledge of those skilled in the art based on the teachings herein. For use in the assay methods disclosed herein, mammalian, especially human, cells are preferred.

More particularly, the present invention also includes recombinant constructs comprising one or more of the sequences as broadly described above. The constructs comprise a vector, such as a plasmid or viral vector, especially where the Baculovirus/SF9 vector/expression system is used, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)). A preferred embodiment utilizes expression from insect cells, especially SF9 cells from *Spodoptera frugiperda*.

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), *Recombinant Gene Expression Protocols*, in *Methods in Molecular Biology*, Vol. 62, (Tuan, ed., Humana Press, Totowa, N.J., 1997), and *Current Protocols in Molecular Biology*, (Ausabel et al, Eds., ), John Wiley & Sons, NY (1994-1999), the disclosures of which are hereby incorporated by reference in their entirety.

Transcription of the DNA encoding the polypeptides of the present invention by eukaryotic cells, especially mammalian cells, most especially human cells, is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* Trp1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Use of a Baculovirus-based expression system is a preferred and convenient method of forming the recombinants disclosed herein. Baculoviruses represent a large family of DNA viruses that infect mostly insects. The prototype is the nuclear polyhedrosis virus (AcMNPV) from *Autographa californica*, which infects a number of lepidopteran species. One advantage of the baculovirus system is that recombinant baculoviruses can be produced in vivo. Following co-transfection with transfer plasmid, most progeny tend to be wild type and a good deal of the subsequent processing involves screening. To help identify plaques, special systems are available that utilize deletion mutants. By way of non-limiting example, a recombinant AcMNPV derivative (called Bac-PAK6) has been reported in the literature that includes target sites for the restriction nuclease Bsu36l upstream of the polyhedrin gene (and within ORF 1629) that encodes a capsid gene (essential for virus viability). Bsf36l does not cut elsewhere in the genome and digestion of the BacPAK6 deletes a portion of the ORF1629, thereby rendering the virus non-viable. Thus, with a protocol involving a system like Bsu36l-cut BacPAK6 DNA most of the progeny are non-viable so that the only progeny obtained after co-transfection of transfer plasmid and digested BacPAK6 is the recombinant because the transfer plasmid, containing the exogenous DNA, is inserted at the Bsu36l site thereby rendering the recombinants resistant to the enzyme. [see Kitts and Possee, A method for producing baculovirus expression vectors at high frequency, *BioTechniques*, 14, 810-817 (1993). For general procedures, see King and Possee, *The Baculovirus Expression System: A Laboratory Guide*, Chapman and Hall, New York (1992) and *Recombinant Gene Expression Protocols*, in *Methods in Molecular Biology*, Vol. 62, (Tuan, ed., Humana Press, Totowa, N.J., 1997), at Chapter 19, pp. 235-246.

In accordance with the foregoing, the present invention further relates to vectors comprising a polynucleotide of the invention and to recombinant eukaryotic cells expressing the stearoyl-CoA desaturase of the present invention, preferably wherein said cell is a mammalian cell, most preferably a human cell.

The present invention further relates to processes for using the polynucleotides, enzymes, and cells disclosed herein in a process for determining the ability of an agent to modulate the expression of said human stearoyl-CoA desaturase in cells expressing said human stearoyl-CoA desaturase of the invention, comprising the steps of:

(a) contacting the agent under suitable conditions with a eukaryotic cell expressing the human stearoyl-CoA desaturase of the invention at a predetermined level of said agent;

(b) determining if the expression level of said stearoyl-CoA desaturase changes after said contact, thereby determining if said agent has modulated said expression level.

In one such embodiment, the present invention relates to a process for identifying a compound that modulates the biological activity of a human stearoyl-CoA desaturase 5 (hSCD5), comprising:

(a) contacting a compound with a cell expressing the human stearoyl-CoA desaturase of the invention under conditions promoting said expression, and (b) detecting a difference in expression of said desaturase as compared to when said compound is not present, thereby identifying a compound that modulates human desaturase biological activity.

In specific embodiments, said modulation is an increase in said expression level or a decrease in said expression level and the cells employed may be mammalian cells, especially human cells, including the recombinant cells disclosed herein. Said cells may also be recombinant cells genetically engineered to produce the desaturase of the invention, such as where a polynucleotide of the invention is inserted into such cell, for example, using one of the vectors disclosed herein. In one such embodiment, the cell is engineered to contain more than one such gene expressing hSCD5. In a separate embodiment, the recombinant cell may not otherwise express such a gene, such as where the cell does not normally contain such a gene as part of its genetic complement but is specifically engineered to contain, and to express, such a gene, thereby expressing hSCD5. In accordance with the present invention, said expression level may be determined by determining the level of messenger RNA produced after contact of said cell with said agent The difference in the expression levels so measured may involve a difference in the overall amount of polypeptide or mRNA produced from a given gene or the rate of said production over time.

Factors that may modulate gene expression include transcription factors such as, but not limited to, retinoid X receptors (RXRs), peroxisomal proliferation-activated receptor (PPAR) transcription factors, the steroid response element binding proteins (SREBP-1 and SREBP-2), REV-ERBα, ADD-1, EBPα, CREB binding protein, P300, HNF 4, RAR, LXR, and RORα.

Physiological benefits of an increase or decrease in the activity or expression of hSCD5 include, but are not limited to, increased plasma HDL and/or decreased triglycerides leading to cardioprotective benefit, therapeutic benefit in Type II diabetes, weight loss, and decreased chance of malignancy. Thus, the determination of the ability of agents to modulate such activity or expression affords an opportunity to discover useful therapeutic agents producing such effects.

In addition, variations in hSCD5 gene expression, function, stability, catalytic activity and other characteristics may be due to allelic variations in the polynucleotide sequences encoding such enzymes. The processes disclosed according to the present invention may likewise be used to determine such genomic effects on expression of hSCD5. Using the processes of the present invention, such variations may be determined at the level of DNA polymorphism within the hSCD5 gene and/or promoter sequences. Such effects lead to the elucidation of associations between such polymorphisms and predisposition to cancer, neurological disease, skin disease, obesity, diabetes, immune function and lipid metabolism through both population and family-based genetic analysis.

In specific embodiments, the present invention contemplates a process wherein said modulation is an increase or decrease in said expression level and where said cell may be a mammalian cell, especially a human cell, including any of the recombinant cells disclosed herein. In one embodiment, the expression level is determined by determining the level of messenger RNA produced after contact of said cell with said agent.

In another aspect, the present invention relates to a process for determining the ability of an agent to modulate the activity of a human stearoyl-CoA desaturase, comprising the steps of:

(a) contacting the agent under suitable conditions with the human stearoyl-CoA desaturase of the invention at a predetermined level of said agent;

(b) determining if the activity of said stearoyl-CoA desaturase changes after said contact, thereby determining if said agent has modulated said activity.

In one such embodiment, the present invention relates to a process for identifying a compound that modulates hSCD5 biological activity, comprising:

(a) contacting a compound with the human stearoyl-CoA desaturase of the invention in the presence of a lipid that can act as a substrate of said desaturase under conditions promoting desaturation of the lipid by said desaturase, and (b) detecting a difference in the desaturation of said lipid by said desaturase as compared to when said compound is not present, thereby identifying a compound that modulates human stearoyl-CoA desaturase activity.

Such an assay may be carried out as a cell free assay employing a cellular fractional, such as a microsomal fraction, obtained by conventional methods of differential cellular fractionation, most commonly by ultracentrifugation methods. In specific embodiments, such modulation may be an increase or decrease in the activity of the desaturase.

In a further aspect, the present invention relates to a process for determining the ability of an agent to modulate the activity of a human stearoyl-CoA desaturase in cells expressing the human stearoyl-CoA desaturase of the invention, comprising the steps of:

(a) contacting the agent under suitable conditions with a eukaryotic cell expressing the human stearoyl-CoA desaturase of the invention at a predetermined level of said agent and under conditions where said agent may or may not modulate the expression level of said desaturase;

(b) determining if the activity of said stearoyl-CoA desaturase changes after said contact, thereby determining if said agent has modulated said expression level.

In specific embodiments of said processes, the modulation may be an increase or decrease in activity of the desaturase and cells useful in these processes are preferably mammalian cells, most preferably human cells, and include any of the recombinant cells disclosed herein.

This invention teaches screening assays employing hSCD5 for use in identifying prophylactic and/or therapeutic agents for use in treating diseases or conditions, and in particular for use in treating a disease or condition which includes, but is not limited to, cholesterol disorders, lipidemias, cardiovascular disease (including a low HDL disorder or a high triglyceride disorder), diabetes, obesity, weight disorders, kidney dysfunction, baldness, skin diseases, cancer and multiple sclerosis, especially where the disease is a cardiovascular disease or a skin disease or where the condition is baldness. On the basis of the disclosure herein, those skilled in the art are able to develop the claimed screening assays based on known types of assays available. Known types of assays include cell based, cell extract (i.e. microsomal assays) or cell free (i.e. transcription) assays. Such assays are typically radioactivity or fluorescence based (i.e. fluorescence resonance transfer or FRET), or they may measure cell behavior (growth, activity, shape, etc). Alternatively, screening may employ multicellular organisms, including genetically modified organisms such as knock-out or knock-in mice, or naturally occurring genetic variants. Screening assays may be manual or low throughput assays, or they may be high throughput screens which are mechanically/robotically enhanced.

In one such embodiment, the present invention provides a process for identifying a compound that modulates triglyceride levels, comprising administering to an animal an effective amount of a compound identified as a modulator of hSCD5 biological activity using a process of the invention and detecting a difference in the triglyceride level in said animal as compared to when said compound is not administered, thereby identifying a compound that modulates triglyceride levels.

In another such embodiment, the invention provides a process for identifying a compound that modulates cholesterol levels, comprising administering to an animal an effective amount of a compound identified as a modulator of hSCD5 biological activity using a process of the invention and detecting a difference in the cholesterol level in said animal as compared to when said compound is not administered, thereby identifying a compound that modulates cholesterol levels.

The tissues monitored for such activity conveniently include plasma and the animal may be a mammal, especially a human being.

The aforementioned processes afford the basis for screening processes, including high throughput screening processes, for determining the efficacy of potential therapeutic and diagnostic drugs for treating the diseases described herein, preferably diseases in which increased or decreased activity or expression of stearoyl-CoA desaturase (hSCD5 of the invention) plays a key role in mediating such disease.

In accordance with the foregoing, the present invention also relates to therapeutic and/or diagnostic agents, regardless of molecular size or weight, effective in treating and/or diagnosing and/or preventing any of the diseases disclosed herein, preferably where such agents have the ability to modulate activity and/or expression of the hSCD5 disclosed herein, and most preferably where said agents have been determined to have such activity through at least one of the screening assays disclosed according to the present invention. In one specific embodiment said agent is an antibody with specificity for hSCD5 that, when administered to a patient, has the effect of neutralizing said hSCD5 and thereby decreasing the activity of such enzyme.

Thus, in one aspect the present invention relates to agents capable of modulating the activity and/or expression of human stearoyl-CoA desaturase 5 (hSCD5) as disclosed herein, especially where said modulating ability was first determined using an assay of comprising hSCD5 or a gene encoding hSCD5, or an assay which measures hSCD5 activity. As used herein the term "capable of modulating" refers to the characteristic of such an agent whereby said agent has the effect of changing the activity of hSCD5, either by increasing or decreasing said activity, under suitable conditions of temperature, pressure, pH and the like so as to facilitate such modulation to a point where it can be detected either qualitatively or quantitatively and wherein such modulation may occur in either an in vitro or in vivo environment. In addition, while the term "modulation" is used herein to mean a change in activity, more specifically either an increase or decrease in such activity, the term "activity" is not to be limited to specific enzymatic activity alone (for example, as measured in units per milligram or some other suitable unit of specific activity) but includes increases in enzyme activity due not to changes in specific enzyme activity but due to changes (i.e., modulation) of expression of polynucleotides encoding and expressing said hSCD5 enzyme. Human SCD5 activity may also be influenced by agents which bind specifically to substrates of hSCD5. Thus, the term "modulation" as used herein means a change in hSCD5 activity regardless of the molecular genetic level of said modulation, be it an effect on the enzyme per se or an effect on the genes encoding the enzyme or on the RNA, especially mRNA, involved in expression of the genes encoding said enzyme. Thus, modulation by such agents can occur at the level of DNA, RNA or enzyme protein and can be determined either in vivo or ex vivo.

In specific embodiments thereof, said assay is any of the assays disclosed herein according to the invention. In addition, the agent(s) contemplated by the present disclosure includes agents of any size or chemical character, either large or small molecules, including proteins, such as antibodies, nucleic acids, either RNA or DNA, and small chemical structures, such as small organic molecules.

In other aspects, the present invention contemplates agents wherein said agent is useful in treating, preventing and/or diagnosing a disease or condition. Specific embodiments are directed to situations wherein the disease or condition includes, but is not limited to, cholesterol disorders, lipidemias, cardiovascular disease, diabetes, obesity, baldness, skin diseases, cancer, kidney dysfunction, and multiple sclerosis, especially where the disease is a cardiovascular disease or a skin disease or where the condition is baldness. In a preferred embodiment, such agents will increase HDL levels in a patient and/or decrease triglyceride levels in a patient Either or both effects are directly associated with reduced risk of cardiovascular disease and coronary artery disease.

In another aspect the present invention is directed to compositions comprising the polynucleotides, polypeptides or other chemical agents, including therapeutic, prophylactic or diagnostic agents, such as small organic molecules, disclosed herein according to the present invention wherein said polynucleotides, polypeptides or other agents are suspended in a pharmacologically acceptable carrier, which carrier includes any pharmacologically acceptable diluent or excipient.

Thus, the pharmaceutical compositions useful herein also contain a pharmaceutically acceptable carrier, including any suitable diluent or excipient, which includes any pharmaceutical agent that does not induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition).

In another aspect the present invention further relates to a process for preventing or treating a disease or condition in a patient afflicted therewith comprising administering to said patient a therapeutically or prophylactically effective amount of a composition as disclosed herein.

In specific embodiments thereof, disease or condition includes, but is not limited to, cholesterol disorders, lipidemias, cardiovascular disease, diabetes, obesity, baldness, skin diseases, cancer, kidney dysfunction, and multiple sclerosis, especially where said disease is a cardiovascular disease or a skin disease or where said condition is baldness. In a preferred embodiment, such disease or condition is a low HDL level or an elevated triglyceride level in a subject at risk of cardiovascular disease.

In an additional aspect, the present invention also relates to a process for diagnosing a disease or condition in a patient, commonly a human being, suspected of being afflicted therewith, or at risk of becoming afflicted therewith, comprising obtaining a tissue sample from said patient and determining the level of activity of hSCD5 in the cells of said tissue sample and comparing said activity to that of an equal amount of the corresponding tissue from a patient not suspected of being afflicted with, or at risk of becoming afflicted with, said disease or condition. In specific embodiments thereof, said disease or condition includes, but is not limited to, cholesterol disorders, lipidemias, cardiovascular disease, diabetes, obesity, baldness, skin diseases, cancer and multiple sclerosis, especially wherein said disease is a cardiovascular disease or a skin disease or said condition is baldness.

In an additional aspect, this invention teaches that hSCD5 has pharmacogenomic significance. Variants of hSCD5 including SNPs (single nucleotide polymorphisms), cSNPs (SNPs in a cDNA coding region), polymorphisms and the like may have dramatic consequences on a subject's response to administration of a prophylactic or therapeutic agent. Certain variants may be more or less responsive to certain agents. In another aspect, any or all therapeutic agents may have greater or lesser deleterious side-effects depending on the hSCD5 variant present in the subject In general, the invention discloses a process of selecting a prophylactic and/or therapeutic agent for administration to a subject in need thereof comprising, (a) determining at least a part of the hSCD5 nucleic acid sequence of said subject; and (b) comparing said hSCD5 nucleic sequence to known variants of hSCD5 nucleic acids;

wherein said known variants are correlated with responsiveness to said agent and said agent is selected for said subject on the basis of a desired correlation. In this method the correlation may be a prophylactic and/or therapeutic effect or it may be avoidance of a deleterious side effect, or any other desired correlation.

Those skilled in the art are able to confirm the relevance of hSCD5 to human health by analogy to animal models. Models that may be used to ascertain the role of hSCD5 in growth, development, diseases or disease processes include genetically modified multicellular animals, such as knock-out or knock-in mice; and yeast recovery assays, where SCD deficient yeast are recovered by administration of an expression construct bearing the hSCD5 gene.

The present invention also relates to a process that comprises a method for producing a product comprising identifying an agent according to one of the disclosed processes for identifying such an agent (i.e., the therapeutic agents identified according to the assay procedures disclosed herein) wherein said product is the data collected with respect to said agent as a result of said identification process, or assay, and wherein said data is sufficient to convey the chemical character and/or structure and/or properties of said agent For example, the present invention specifically contemplates a situation whereby a user of an assay of the invention may use the assay to screen for compounds having the desired enzyme modulating activity and, having identified the compound, then conveys that information (i.e., information as to structure, dosage, etc) to another user who then utilizes the information to reproduce the agent and administer it for therapeutic or research purposes according to the invention. For example, the user of the assay (user 1) may screen a number of test compounds without knowing the structure or identity of the compounds (such as where a number of code numbers are used the first user is simply given samples labeled with said code numbers) and, after performing the screening process, using one or more assay processes of the present invention, then imparts to a second user (user 2), verbally or in writing or some equivalent fashion, sufficient information to identify the compounds having a particular modulating activity (for example, the code number with the corresponding results). This transmission of information from user 1 to user 2 is specifically contemplated by the present invention.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLE 1

Expression Analysis of Human SCD5 Transcripts in Multiple Human Tissues.

Methods: A 627 bp EcoRI/Hind III fragment of the human SCD5 cDNA was restricted from EST clone AW131469. This corresponds to a 5' region of the cDNA, including the initiating ATG. This region of the cDNA was chosen to maximize sequence divergence between human SCD1 and SCD5 so as to avoid cross hybridization. The probe was labeled by RediPrimer II according to the manufactures instructions with alpha-[$^{32}$P]dCTP supplied by NEN. The labeled probes were purified with Centri·Sep spin columns from Princeton Separation Inc. For the Northern Blot, the Human 12-lane MTN Blot cat# 7780-1 from Clontech was used with the ExpressHyb protocol. Labeled blots were exposed to minus 70 degrees for an average of 17 hours.

Results of the hSCD5 northern blot are shown in FIG. 5. Human tissues analyzed were brain, heart, skeletal muscle, colon, thymus, spleen, kidney, liver, small intestine, placenta, lung and leukocyte. The expected transcript size for human SCD5 is 3.0 kb, based on characterization of the cDNA. A 3.0 kb transcript was detected and expressed fairly ubiquitously, with the highest levels of expression in the brain and kidney. A larger 4.5 kb transcript was also observed. This may reflect a differentially spliced SCD5 transcript or cross hybridization with other desaturases. Notably, hSCD5 was not highly expressed in the liver.

Transcripts identified with the SCD5 probe are unlikely to correspond to SCD1. Published transcript sizes for SCD1 are 3.9 kb and 5.2 kb. A comparison blot was also performed with an SCD1 cDNA, confirming published reports of widespread expression with the highest levels in the liver and the brain.

EXAMPLE 2

Transfection of Cells with hSCD5 Construct Leads to Significant Gain in Delta-9-Desaturase Activity Methods: A human SCD5 construct was created using a vector for mammalian expression, pcDNA3.1N5-His-TOPO. The cDNA coding for hSCD5 was amplified by PCR from hSCD5 EST A1815730 using primers hSCD5pcDNA3.1F (caccatgccaggcccggccaccga; SEQ ID NO:13) and hSCD5pcDNA3.1R (agcactgctgtccagtcc; SEQ ID NO:14). PCR was carried out using Stratagene's Herculase™ Hot-start DNA Polymerase. Amplified PCR product was run out on a TAE gel and purified by GENECLEAN SPIN Kit cat#1101-200. The amplified PCR product of the hSCD5 fragment was ligated into the mammalian expression vector pcDNA3.1/V5-His-TOPO® supplied by Invitrogen and transformed into NovaBlue Singles™ from Novagen, according to the manufactures instructions. Plasmids were isolated by Qiagen's MiniPrep protocol and their inserts were sequenced using standard T7 primers internal primers. The correct orientation and sequence of the cloned hSCD5 constructs were verified by restriction digestion and sequence analysis.

This construct was transfected into human 293K cells (or HEK 293 cells) which are known to demonstrate low intrinsic delta-9 desaturase activity. Confluent cells were split in ¼ in DMEM with 10% FBS into small plates with 20 ml media. Prior to transfection, media was replaced with fresh media, with 10 ul 5 mM chloroquine. After chloroquine was added 2 mll transfection mixture, including 20 ug hSCD5/Topo construct DNA was added to the media ($H_2O$; 450 μl-μl DNA added DNA; 10 μl pCMV-Lac; 500 μl 2× HBS buffer 500 μl; 50 μl 2.5 M$CaCl_2$). Cells were incubated at 37° C. for 6 hours, prior to aspiration of media and addition of 20 ml fresh media. Cells were incubated for an additional 48 hours at 37° C. Transfection efficiency was judged based on LacZ staining. Controls employed were maximally induced mouse liver microsomes (having increased SCD1 activity), and HEK 293 cells with or without mock transfection. Cells were washed 2× with PBS and then scraped off plates in 10 ml PBS. Cells were centrifuged at 1200 prm for 10 min at 4° C. PBS was aspirated and cells were resuspended in 1 ml of fresh PBS and transferred to an eppendorf. A small aliquot of suspended cells was removed to test for expression of SCD5 by Western blot. The remainder of the cells were centrifuged at 1200 rpm for 10 min, 4° C. PBS was aspirated and the cell pellet was frozen and stored at −70° C. prior to the microsomal preparation.

Figure 6:
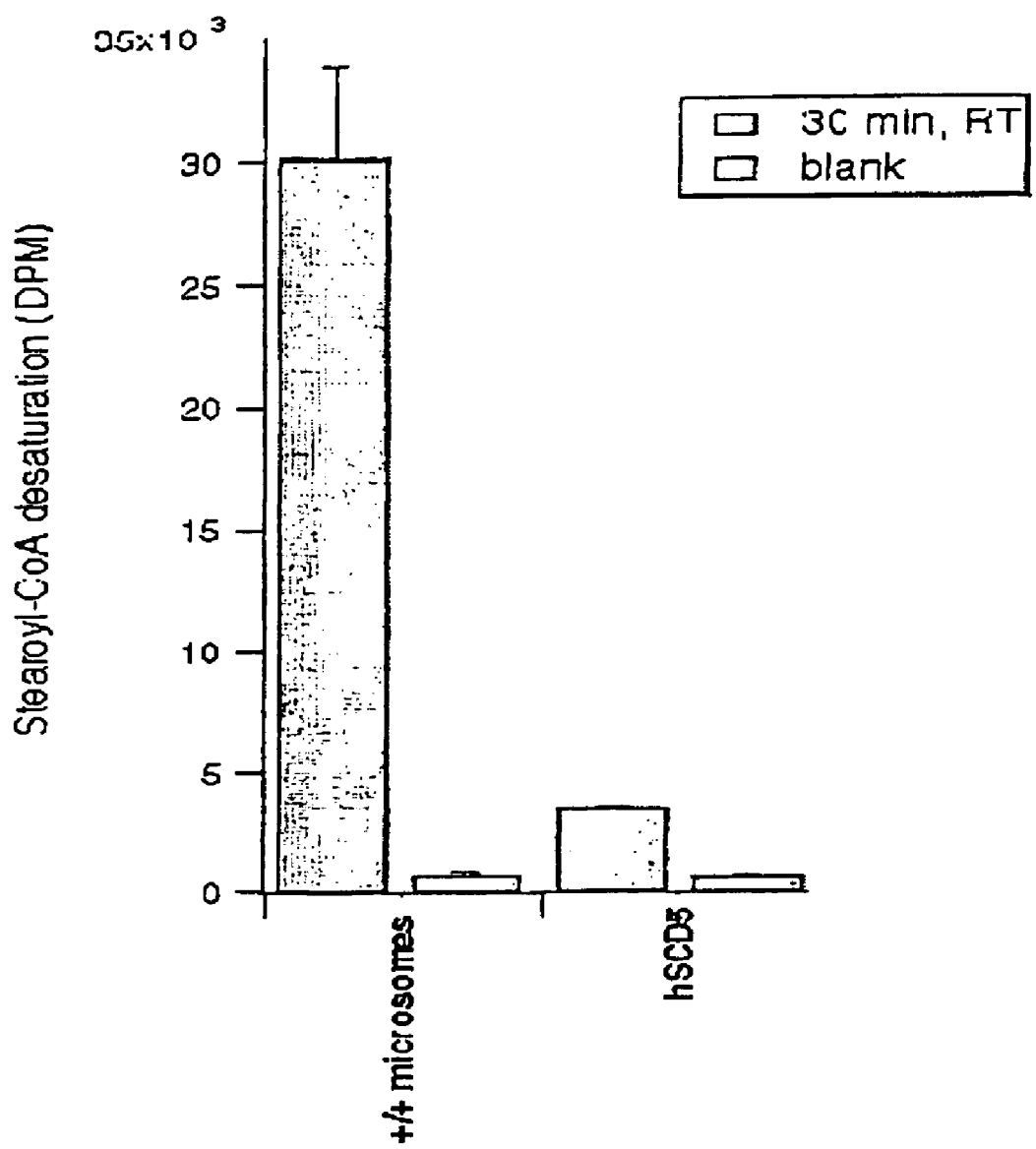
FIG. 6 demonstrates that delta-9 desaturase activity is substantially increased in cells transfected with hSCD5 cDNA, thus confirming the functional role of hSCD5 as a delta-9 desaturase.

In all cases, the microsomal assay used to measure delta-9-desaturase biological activity was the tritium desaturation assay set out in WO 01/62954. Basically, the assay measures the release of tritium from stearoyl-CoA having tritium incorporated at C9 and C10. Cell pellets were homogenized using a motorized Potter-Elvehjem homogenizer on an intermediate power setting so as not to overheat preparation. Cells were homogenized for 1 min in 0.1 M PK buffer on ice. Homogenate was spun for 15 min, 10,000×g, 4° C. Supernatant was transferred to a clean tube and the pellet material was discarded. Microsome solution was centrifuged for 60 min, 100,000×g, 4° C. Supernatant was discarded and pellet, containing microsomes, was rinsed with 1 ml of cold 0.1 M PK buffer. PK buffer was removed and pellet was resuspended in cold 0.1 M PK buffer (2 μl/mg cell pellet). Microsome solution was transferred to tube and rehomogenized for 1min at an intermediate setting. Protein concentration was determined and microsomes diluted to yield a concentration of 20 mg/ml. The Activity assay pre-mix contains 2 μl 1.5 mM stearoyl-CoA (0.03 mM final), 1 μl 1 mCi/ml radioactive $^3$H stearoyl-CoA (1 μl), 10 μl 20 mM NADH (2 mM final), 67 μl 0.1 M PK buffer per assay point. Assay pre-mix (80 μl/assay point) was added 20 μl of microsomes to initiate reaction. Reaction proceeded at room temperature for 30 minutes. Reactions were then quenched with 10 μl of 6% PCA. Following vortexing, 100 μl of charcoal suspension was added to sediment the unused substrate. Following vortexing, samples were centrifuged at 13,000 rpm, 10 min, 4° C. 50 μl supernatant was removed and transferred to a counting vial for liquid scintillation counting Results are shown in FIG. 6. The results show that transient expression of human SCD5 in HEK 293 cells can increase delta-9 desaturase activity significantly above mock transfected HEK 293 cells. The increase in activity is substantial, amounting to about 10% of that measured in maximally induced mouse liver microsomes.

In applying the disclosure, it should be kept clearly in mind that other and different embodiments of the methods disclosed according to the present invention will no doubt suggest themselves to those of skill in the relevant art.

REFERENCE LIST

1. Mihara, K. Structure and regulation of rat liver microsomal stearoyl-CoA desaturase gene. *J. Biochem.* (Tokyo). 108, 1022-1029 (1990).
2. Thiede, M. A. & Strittmatter, P. The induction and characterization of rat liver stearyl-CoA desaturase mRNA. *J. Biol. Chem.* 260, 14459-14463 (1985).
3. Kaestner, K. H., Ntambi, J. M., Kelly, T. J., Jr. & Lane, M. D. Differentiation-induced gene expression in 3T3-L1 preadipocytes. A second differentially expressed gene encoding stearoyl-CoA desaturase. *J. Biol. Chem.* 264, 14755-14761 (1989).
4. Ntambi, J. M. et aL Differentiation-induced gene expression in 3T3-L1 preadipocytes. Characterization of a differentially expressed gene encoding stearoyl-CoA desaturase. *J. Biol. Chem.* 263, 17291-17300 (1988).
5. Zhang, L., Ge, L, Parimoo, S., Stenn, K. & Prouty, S. M. Human stearoyl-CoA desaturase: alternative transcripts generated from a single gene by usage of tandem polyadenylation sites. *Biochem. J.* 340 (Pt 1), 255-264 (1999).
6. Zheng, Y. et al. Scd 1 is expressed in sebaceous glands and is disrupted in the asebia mouse [letter]. *Nat Genet.* 23, 268-270 (1999).
7. Sundberg, J. P. et aL Asebia-2J (Scd1(ab2J)): a new allele and a model for scarring alopecia. *Am. J. Pathol.* 156, 2067-2075 (2000).
8. Miyazaki, M., Kim, Y. C., Keller, M. P., Attie, A. D. & Ntambi, J. M. The biosynthesis of hepatic cholesterol esters and triglycerides is impaired in mice with a disruption of the gene for stearoyl-CoA desaturase 1. *J. Biol. Chem.* (2000).

9. Spector, A. A. & Yorek, M. A. Membrane lipid composition and cellular function. *J. Lipid Res.* 26, 1015-1035 (1985).
10. Enser, M. & Roberts, J. L. The regulation of hepatic stearoyl-coenzyme A desaturase in obese-hyperglycaemic (ob/ob) mice by food intake and the fatty acid composition of the diet. *Biochem. J.* 206, 561-570 (1982).
11. Enser, M. The role of insulin in the regulation of stearic acid desaturase activity in liver and adipose tissue from obese-hyperglycaemic (ob/ob) and lean mice. *Biochem. J.* 180, 551-558 (1979).
12. Enser, M. Desaturation of stearic acid by liver and adipose tissue from obese-hyperglycaemic mice (ob/ob). *Biochem. J.* 148, 551-555 (1975).
13. Jones, B. H. et al Adipose tissue stearoyl-CoA desaturase mRNA is increased by obesity and decreased by polyunsaturated fatty acids. *Am. J. Physiol* 271, E44-E49 (1996).
14. Kim, Y. C., Gomez, F.E., Fox, B. G. & Ntambi, J. M. Differential regulation of the stearoyl-CoA desaturase genes by thiazolidinediones in 3T3-L1 adipocytes. *J. Lipid Res.* 41, 1310-1316 (2000).
15. Li, J. et aL. Partial characterization of a cDNA for human stearoyl-CoA desaturase and changes in its mRNA expression in some normal and malignant tissues. *Int. J. Cancer* 57, 348-352 (1994).
16. Wood, C. B. et al. Reduction in the stearic to oleic acid ratio in human malignant liver neoplasms. *Eur. J. Surg. Oncol.* 11, 347-348 (1985).
17. Habib, N.A. et al. Stearic acid and carcinogenesis. *Br. J. Cancer* 56, 455-458 (1987).
18. Tronstad, K. J., Berge, K., Bjerkvig, R., Flatmark, T. & Berge, R.K. Metabolic effects of 3-thia fatty acid in cancer cells. *Adv. Exp. Med. Biol.* 466, 201-204 (1999).
19. DeWille, J. W. & Farmer, S. J. Postnatal dietary fat influences mRNAS involved in myelination. *Dev. Neurosci.* 14, 61-68 (1992).
20. Garbay, B. et al. Regulation of oleoyl-CoA synthesis in the peripheral nervous system: demonstration of a link with myelin synthesis. *J. Neurochem.* 71, 1719-1726 (1998).
21. Marcelo, C. L, Duell, E. A., Rhodes, L. M. & Dunham, W. R. In vitro model of essential fatty acid deficiency. *J. Invest Dermatol.* 99, 703-708 (1992).
22. Tebbey, P. W. & Buttke, T. M. Stearoyl-CoA desaturase gene expression in lymphocytes [published erratum appears in Biochem Biophys *Res Commun* 1992 Sep. 16;187(2):1201]. *Biochem. Biophys. Res. Commun.* 186, 531-536 (1992).
23. Tebbey, P. W. & Buttke, T. M. Molecular basis for the immunosuppressive action of stearic acid on T cells [published erratum appears in Immunology 1990 October; 71(2):306]). *Immunology* 70, 379-386 (1990).
24. Stampfer et al. A prospective study of cholesterol, apolipoproteins, and the risk of myocardial infraction. *N. Engl. J. Med.* 325, 373-381 (1991).
25. Schmidt et al. Clustering of dyslipidemia, hyperuricemia, diabetes, and hypertension and its association with fasting insulin and central and overall obesity in a general population. Atherosclerosis Risk in Communities Study Investigators *Metabolism* 45 (6):699-706 (1996).
26. Park et aL Inhibition of hepatic stearoyl-CoA desaturase activity by trans-10,cis-12 conjugated linoleic acid and its derivatives. Biochim Biophys Acta. 1486(2-3):285-92 (2000).
27. Choi et al. The trans-10, cis-12 isomer of conjugated linoleic acid downregulates stearoyl-CoA desaturase 1 gene expression in 3T3-L1 adipocytes. *J Nutr.* 130(8): 1920-4 (2000).

What is claimed is:

1. A method for treating low HDL levels or elevated triglyceride levels in a patient afflicted therewith, comprising administering to said patient an agent that modulates desaturase activity of a human stearoyl-CoA desaturase 5 (hSCD5) having the amino acid sequence of SEQ ID NO: 2 wherein said agent is administered in an amount sufficient to decrease hSCD5 desaturase activity in said patient.

2. The method of claim 1, wherein said activity is enzyme activity.

3. The method of claim 1, wherein said activity is expression of a polynucleotide encoding hSCD1 polypeptide.

4. The method of claim 3, wherein said expression is gene transcription.

5. The method of claim 1, wherein said agent modulates a transcription factor.

6. The method of claim 1, wherein said agent is selected from the group consisting of retinoid X receptors (RXRs), peroxisomal proliferation-activated receptor (PPAR) transcription factors, the steroid response element binding proteins (SREBP-1 and SREBP-2), REV-ERBα, ADD-1, EBPα, CREB binding protein, P300, HNF 4, RAR, LXR, and RORα.

* * * * *

UNITED STATES PATENT AND TRADEMARK OFFICE
CERTIFICATE OF CORRECTION

PATENT NO. : 7,435,559 B2
APPLICATION NO. : 11/810057
DATED : October 14, 2008
INVENTOR(S) : Alison J. Brownlie It is certified that error appears in the above-identified patent and that said Letters Patent is hereby corrected as shown below:

At column 17, line 19, delete "N5" and insert therefor --/ V5--

At column 17, line 42, delete "5 mM" and insert therefor --50 mM--

At column 17, line 45, delete "10 µl" and insert therefor --10 µg--

At column 18, line 15, delete "1 µl" and insert therefor --1 µCi--

Signed and Sealed this

Tenth Day of March, 2009

JOHN DOLL
*Acting Director of the United States Patent and Trademark Office*

SEQUENCE LISTING

<160> NUMBER OF SEQ ID NOS: 14

<210> SEQ ID NO 1
<211> LENGTH: 3042
<212> TYPE: DNA
<213> ORGANISM: Homo sapiens

<400> SEQUENCE: 1

```
gaattcggca cgaggttcag cccgggcagc catatggggg atacgccagc aacagacgcc      60
ggccgccaag atctgcatcc ctaggccacg ctaagaccct ggggaagagc gcaggagccc     120
gggagaaggg ctggaaggag gggactggac gtgcggagaa ttcccccta aaaggcagaa      180 gcccccgccc ccaccctcga gctccgctcg ggcagagcgc ctgcctgcct gccgctgctg     240
cgggcgccca cctcgcccag ccatgccagg cccgccacc gacgcgggga agatcccttt      300
ctgcgacgcc aaggaagaaa tccgtgccgg gctcgaaagc tctgagggcg gcggcggccc     360
ggagaggcca ggcgcgcgcg ggcagcggca gaacatcgtc tggaggaatg tcgtcctgat     420
gagcttgctc cacttggggg ccgtgtactc cctggtgctc atcccaaag ccaagccact      480 cactctgctc tgggcctact tctgcttcct cctggccgct ctgggtgtga cagctggtgc     540
ccatcgcttg tggagccaca ggtcctaccg ggccaagctg cctctgagga tatttctggc     600
tgtcgccaac tccatggctt tccagaatga catcttcgag tggtccaggg accaccgagc     660
```

```
ccaccacaag tactcagaga cggatgctga cccccacaat gcccgccggg gcttcttctt    720
ctcccatatt gggtggctgt tgttcgcaa gcatcgagat gttattgaga agggagaaa     780
gcttgacgtc actgacctgc ttgctgatcc tgtggtccgg atccagagaa agtactataa   840
gatctccgtg gtgctcatgt gctttgtggt ccccacgctg gtgccctggt acatctgggg  900
agagagtctg tggaattcct acttcttggc ctctattctc cgctatacca tctcactcaa  960
catcagctgg ctggtcaaca gcgccgccca catgtatgga aaccggccct atgacaagca  1020
catcagccct cggcagaacc cactcgtcgc tctgggtgcc attggtgaag cttccataa   1080
ttaccatcac acctttccct ttgactactc tgcgagtgaa tttggcttaa attttaaccc  1140
aaccacctgg ttcattgatt tcatgtgctg gctggggctg gccactgacc gcaaacgggc  1200
aaccaagccg atgatcgagg cccggaaggc caggactgga gacagcagtg cttgaacttg  1260
gaacagccat cccacatgtc tgccgttgca acctcggttc atggctttgg ttacaatagc  1320
tctcttgtac attggatcgt ggggaggggc agagggtggg gaaggaacga gtcaatgtgg  1380
tttgggaatg ttttgtttta ctcaaaata tgttgaaat acaattatca atgaaaaaac    1440
tttcgttttt tttttgttt gttttgtttt tgagacagag tctcactctg tcacccaggc  1500
tggagtgcag tggcgcagtc tcggctcact gcagcctcca cctacctggt tcaagcaatt  1560
ctcctgcctc agcctcctga gtagctgaga ttacaggagc ctgccaccac acccagctaa  1620
ttttttttgta tttttagtag agacagggtt tcatcatgtt ggccagactg gcctcgaatt  1680
cctgacctca ggcaatccac ccgcctcggc ctcccaaaga gctgggatta caggcgtgag  1740
ccaccgcacc ctgccgaaaa aaactttttt tttttgaga cggaggctcg ctctgtcccc  1800
caggctggag tgcagtggcg agatctcagc tcactgcaag ctccgcctcc cgggttcacg  1860
ccattctcct gcctcagcct cccgagtagc tgggagccag cgcgcccagc taaaaaaact  1920
tttcaagtca atattactac gatttaacat tagagtgtgg acatgtgatt taatcgctat  1980
agctaaaata cgtcaaatat acgttgtcat gtgcttgaac atgatgctaa ccctgacagg  2040
atgaaggaaa gtaatattct ttcagtgtag ttcaggagag catttgtttt cttttctacc  2100
aattaaccca tcattgcttt taaacaacca tctgaaggag cagagaggca gggtagaaga  2160
cagaaggggg atctatgtgg taactaaaga atgtttctgt tttgttaatt attgtgtgtg  2220
tgtggtttta ttgtttgctt aagagaatca aaaactgaaa aaaatgagaa tacaggaaat  2280
ggctcttgtt tatttttttg ctgtgtttac agcttgttaa tgctctactg tctttgtttc  2340
aagagagatt tgttcactgc ccagctcgtt ttgtgtcctg agcccatgg ccagcccacc  2400
ttataaatca tgcctgttta gatgtttgat tttgttctgt ttgctattgt tatcttaaag  2460
gtgtataact ctgacatgcc agacatcaaa ttaagctcaa attaagctct cgtttaaatg  2520
tttaagcacc taatttatat tctaattgat cccagccact gatgcatgta ctttagctac  2580
ttctgctaaa taagcatatt aattttccac atcagaccat cagatcttga gaaccaacag  2640
ttatctagaa ttccgtgtct actaatgttt cacctgcatg cagccttcat taattttgta  2700
gcaaaatata aagtgatcat tatgtagctt ctggattaaa aaaatttgtg tgtgaagttg  2760
ctttgtaaag tgcatgtgga attaatggga cagtgtgccc tttgtgttag atgttagagc  2820
aaaagaaagg gcttatagtg ttagtattgg agcactttga agatagatat tttcagaaaa  2880
gatgtaggat ttaaaagtta aattttaaat tttagaaaaa gatatgatgg caattggaaa  2940
tagtcacaat gaagttcttc atccagtagg tgttaacag tgttattttg ccactggtaa   3000
tgtgtaaact gtgagtgatt tacaataaat gattatgaat tc                     3042
```

<210> SEQ ID NO 2
<211> LENGTH: 330
<212> TYPE: PRT
<213> ORGANISM: Homo sapiens

<400> SEQUENCE: 2

```
Met Pro Gly Pro Ala Thr Asp Ala Gly Lys Ile Pro Phe Cys Asp Ala
1               5                   10                  15

Lys Glu Glu Ile Arg Ala Gly Leu Glu Ser Ser Glu Gly Gly Gly Gly
                20                  25                  30

Pro Glu Arg Pro Gly Ala Arg Gly Gln Arg Gln Asn Ile Val Trp Arg
            35                  40                  45

Asn Val Val Leu Met Ser Leu Leu His Leu Gly Ala Val Tyr Ser Leu
    50                  55                  60

Val Leu Ile Pro Lys Ala Lys Pro Leu Thr Leu Leu Trp Ala Tyr Phe
65                  70                  75                  80

Cys Phe Leu Leu Ala Ala Leu Gly Val Thr Ala Gly Ala His Arg Leu
                85                  90                  95

Trp Ser His Arg Ser Tyr Arg Ala Lys Leu Pro Leu Arg Ile Phe Leu
            100                 105                 110

Ala Val Ala Asn Ser Met Ala Phe Gln Asn Asp Ile Phe Glu Trp Ser
        115                 120                 125

Arg Asp His Arg Ala His His Lys Tyr Ser Glu Thr Asp Ala Asp Pro
    130                 135                 140

His Asn Ala Arg Arg Gly Phe Phe Phe Ser His Ile Gly Trp Leu Phe
145                 150                 155                 160

Val Arg Lys His Arg Asp Val Ile Glu Lys Gly Arg Lys Leu Asp Val
                165                 170                 175

Thr Asp Leu Leu Ala Asp Pro Val Val Arg Ile Gln Arg Lys Tyr Tyr
            180                 185                 190

Lys Ile Ser Val Val Leu Met Cys Phe Val Val Pro Thr Leu Val Pro
        195                 200                 205

Trp Tyr Ile Trp Gly Glu Ser Leu Trp Asn Ser Tyr Phe Leu Ala Ser
    210                 215                 220

Ile Leu Arg Tyr Thr Ile Ser Leu Asn Ile Ser Trp Leu Val Asn Ser
225                 230                 235                 240

Ala Ala His Met Tyr Gly Asn Arg Pro Tyr Asp Lys His Ile Ser Pro
                245                 250                 255

Arg Gln Asn Pro Leu Val Ala Leu Gly Ala Ile Gly Glu Gly Phe His
            260                 265                 270

Asn Tyr His His Thr Phe Pro Phe Asp Tyr Ser Ala Ser Glu Phe Gly
        275                 280                 285

Leu Asn Phe Asn Pro Thr Thr Trp Phe Ile Asp Phe Met Cys Trp Leu
    290                 295                 300

Gly Leu Ala Thr Asp Arg Lys Arg Ala Thr Lys Pro Met Ile Glu Ala
305                 310                 315                 320

Arg Lys Ala Arg Thr Gly Asp Ser Ser Ala
                325                 330
```

<210> SEQ ID NO 3
<211> LENGTH: 355
<212> TYPE: PRT
<213> ORGANISM: mouse

<400> SEQUENCE: 3

Met Pro Ala His Met Leu Gln Glu Ile Ser Ser Tyr Thr Thr Thr
1               5                   10                  15

Thr Thr Ile Thr Ala Pro Pro Ser Gly Asn Glu Arg Glu Lys Val Lys
            20                  25                  30

Thr Val Pro Leu His Leu Glu Glu Asp Ile Arg Pro Glu Met Lys Glu
            35                  40                  45

Asp Ile His Asp Pro Thr Tyr Gln Asp Glu Gly Pro Pro Lys
50                  55                  60

Leu Glu Tyr Val Trp Arg Asn Ile Ile Leu Met Val Leu Leu His Leu
65                  70                  75                  80

Gly Gly Leu Tyr Gly Ile Ile Leu Val Pro Ser Cys Lys Leu Tyr Thr
                85                  90                  95

Ala Leu Phe Gly Ile Phe Tyr Tyr Met Thr Ser Ala Leu Gly Ile Thr
            100                 105                 110

Ala Gly Ala His Arg Leu Trp Ser His Arg Thr Tyr Lys Ala Arg Leu
            115                 120                 125

Pro Leu Arg Ile Phe Leu Ile Ile Ala Asn Thr Met Ala Phe Gln Asn
130                 135                 140

Asp Val Tyr Asp Trp Ala Arg Asp His Arg Ala His His Lys Phe Ser
145                 150                 155                 160

Glu Thr His Ala Asp Pro His Asn Ser Arg Arg Gly Phe Phe Phe Ser
                165                 170                 175

His Val Gly Trp Leu Leu Val Arg Lys His Pro Ala Val Lys Glu Lys
            180                 185                 190

Gly Gly Lys Leu Asp Met Ser Asp Leu Lys Ala Glu Lys Leu Val Met
            195                 200                 205

Phe Gln Arg Arg Tyr Tyr Lys Pro Gly Leu Leu Met Cys Phe Ile
            210                 215                 220

Leu Pro Thr Leu Val Pro Trp Tyr Cys Trp Gly Glu Thr Phe Val Asn
225                 230                 235                 240

Ser Leu Phe Val Ser Thr Phe Leu Arg Tyr Thr Leu Val Leu Asn Ala
                245                 250                 255

Thr Trp Leu Val Asn Ser Ala Ala His Leu Tyr Gly Tyr Arg Pro Tyr
            260                 265                 270

Asp Lys Asn Ile Gln Ser Arg Glu Asn Ile Leu Val Ser Leu Gly Ala
            275                 280                 285

Val Gly Glu Gly Phe His Asn Tyr His His Thr Phe Pro Phe Asp Tyr
290                 295                 300

Ser Ala Ser Glu Tyr Arg Trp His Ile Asn Phe Thr Thr Phe Phe Ile
305                 310                 315                 320

Asp Cys Met Ala Ala Leu Gly Leu Ala Tyr Asp Arg Lys Lys Val Ser
                325                 330                 335

Lys Ala Thr Val Leu Ala Arg Ile Lys Arg Thr Gly Asp Gly Ser His
            340                 345                 350

Lys Ser Ser
        355

<210> SEQ ID NO 4
<211> LENGTH: 358
<212> TYPE: PRT
<213> ORGANISM: mouse

<400> SEQUENCE: 4

Met Pro Ala His Ile Leu Gln Glu Ile Ser Gly Ala Tyr Ser Ala Thr

```
         1               5                   10                  15
Thr Thr Ile Thr Ala Pro Pro Ser Gly Gly Gln Gln Asn Gly Gly Glu
                20                  25                  30

Lys Phe Glu Lys Ser Ser His His Trp Gly Ala Asp Val Arg Pro Glu
                35                  40                  45

Leu Lys Asp Asp Leu Tyr Asp Pro Thr Tyr Gln Asp Glu Gly Pro
                50                  55                  60

Pro Pro Lys Leu Glu Tyr Val Trp Arg Asn Ile Ile Leu Met Ala Leu
65                  70                  75                  80

Leu His Leu Gly Ala Leu Tyr Gly Ile Thr Leu Val Pro Ser Cys Lys
                85                  90                  95

Leu Tyr Thr Cys Leu Phe Ala Tyr Leu Tyr Val Ile Ser Ala Leu
                100                 105                 110

Gly Ile Thr Ala Gly Ala His Arg Leu Trp Ser His Arg Thr Tyr Lys
                115                 120                 125

Ala Arg Leu Pro Leu Arg Leu Phe Leu Ile Ile Ala Asn Thr Met Ala
                130                 135                 140

Phe Gln Asn Asp Val Tyr Glu Trp Ala Arg Asp His Arg Ala His His
145                 150                 155                 160

Lys Phe Ser Glu Thr His Ala Asp Pro His Asn Ser Arg Arg Gly Phe
                165                 170                 175

Phe Phe Ser His Val Gly Trp Leu Leu Val Arg Lys His Pro Ala Val
                180                 185                 190

Lys Glu Lys Gly Gly Lys Leu Asp Met Ser Asp Leu Lys Ala Glu Lys
                195                 200                 205

Leu Val Met Phe Gln Arg Arg Tyr Tyr Lys Pro Asp Leu Leu Leu Met
                210                 215                 220

Cys Phe Val Leu Pro Thr Leu Val Pro Trp Tyr Cys Trp Gly Glu Thr
225                 230                 235                 240

Phe Val Asn Ser Leu Cys Val Ser Thr Phe Leu Arg Tyr Ala Val Val
                245                 250                 255

Leu Asn Ala Thr Trp Leu Val Asn Ser Ala Ala His Leu Tyr Gly Tyr
                260                 265                 270

Arg Pro Tyr Asp Lys Asn Ile Ser Ser Arg Glu Asn Ile Leu Val Ser
                275                 280                 285

Met Gly Ala Val Gly Glu Arg Phe His Asn Tyr His His Ala Phe Pro
                290                 295                 300

Tyr Asp Tyr Ser Ala Ser Glu Tyr Arg Trp His Ile Asn Phe Thr Thr
305                 310                 315                 320

Phe Phe Ile Asp Cys Met Ala Leu Leu Gly Leu Ala Tyr Asp Arg Lys
                325                 330                 335

Arg Val Ser Arg Ala Ala Val Leu Ala Arg Ile Lys Arg Thr Gly Asp
                340                 345                 350

Gly Ser Cys Lys Ser Gly
        355
```

<210> SEQ ID NO 5
<211> LENGTH: 359
<212> TYPE: PRT
<213> ORGANISM: Homo Sapiens

<400> SEQUENCE: 5

```
Met Pro Ala His Leu Leu Gln Asp Asp Ile Ser Ser Ser Tyr Thr Thr
1               5                   10                  15
```

```
Thr Thr Thr Ile Thr Ala Pro Pro Ser Arg Val Leu Gln Asn Gly Gly
            20                  25                  30

Asp Lys Leu Glu Thr Met Pro Leu Tyr Leu Glu Asp Ile Arg Pro
        35                  40                  45

Asp Ile Lys Asp Ile Tyr Asp Pro Thr Tyr Lys Lys Glu Gly
    50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Tyr Phe Val Ser Ala
            100                 105                 110

Leu Gly Ile Thr Ala Gly Ala His Arg Leu Trp Ser His Arg Ser Tyr
            115                 120                 125

Lys Ala Arg Leu Pro Leu Arg Leu Phe Leu Ile Ile Ala Asn Thr Met
    130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
            165                 170                 175

Phe Phe Phe Ser His Val Gly Trp Leu Leu Val Arg Lys His Pro Ala
            180                 185                 190

Val Lys Glu Lys Gly Ser Thr Leu Asp Leu Ser Asp Leu Glu Ala Glu
            195                 200                 205

Lys Leu Val Met Phe Gln Arg Arg Tyr Tyr Lys Pro Gly Leu Leu Leu
    210                 215                 220

Met Cys Phe Ile Leu Pro Thr Leu Val Pro Trp Tyr Phe Trp Gly Glu
225                 230                 235                 240

Thr Phe Gln Asn Ser Val Phe Val Ala Thr Phe Leu Arg Tyr Ala Val
            245                 250                 255

Val Leu Asn Ala Thr Trp Leu Val Asn Ser Ala Ala His Leu Phe Gly
            260                 265                 270

Tyr Arg Pro Tyr Asp Lys Asn Ile Ser Pro Arg Glu Asn Ile Leu Val
    275                 280                 285

Ser Leu Gly Ala Val Gly Glu Gly Phe His Asn Tyr His His Ser Phe
    290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Leu Gly Leu Ala Tyr Asp Arg
            325                 330                 335

Lys Lys Val Ser Lys Ala Ala Ile Leu Ala Arg Ile Lys Arg Thr Gly
            340                 345                 350

Asp Gly Asn Tyr Lys Ser Gly
        355

<210> SEQ ID NO 6
<211> LENGTH: 327
<212> TYPE: PRT
<213> ORGANISM: carp

<400> SEQUENCE: 6

Met Pro Asp Arg Glu Ile Lys Ser Pro Ile Trp His Pro Glu Pro Gly
1               5                   10                  15

Thr Val Glu Asp Val Phe Asp His Thr Tyr Lys Glu Lys Glu Gly Pro
            20                  25                  30
```

Lys Pro Pro Thr Val Ile Val Trp Arg Asn Val Ile Leu Met Ser Leu
            35                  40                  45

Leu His Leu Gly Ala Leu Tyr Gly Leu Phe Leu Phe Pro Ser Ala Arg
        50                  55                  60

Ala Leu Thr Trp Ile Trp Phe Phe Gly Cys Leu Leu Phe Ser Ala Leu
65                  70                  75                  80

Gly Ile Thr Ala Gly Ala His Arg Leu Trp Ser His Arg Ser Tyr Lys
                85                  90                  95

Ala Ser Leu Pro Leu Gln Ile Phe Leu Ala Leu Gly Asn Ser Met Ala
            100                 105                 110

Phe Gln Asn Asp Ile Tyr Glu Trp Ser Arg Asp His Arg Val His His
            115                 120                 125

Lys Tyr Ser Glu Thr Asp Ala Asp Pro His Asn Ala Val Arg Gly Phe
        130                 135                 140

Phe Phe Ser His Val Gly Trp Leu Leu Val Arg Lys His Pro Asp Val
145                 150                 155                 160

Ile Glu Lys Gly Arg Lys Leu Glu Leu Ser Asp Leu Lys Ala Asp Lys
                165                 170                 175

Val Val Met Phe Gln Arg Arg Phe Tyr Lys Pro Ser Val Leu Leu Met
            180                 185                 190

Cys Phe Phe Val Pro Thr Phe Val Pro Trp Tyr Val Trp Gly Glu Ser
            195                 200                 205

Leu Trp Val Ala Tyr Phe Val Pro Ala Leu Leu Arg Tyr Ala Leu Val
        210                 215                 220

Leu Asn Ala Thr Trp Leu Val Asn Ser Ala Ala His Met Trp Gly Asn
225                 230                 235                 240

Arg Pro Tyr Asp Ser Ser Ile Asn Pro Arg Glu Asn Arg Phe Val Thr
                245                 250                 255

Phe Ser Ala Ile Gly Glu Gly Phe His Asn Tyr His His Thr Phe Pro
            260                 265                 270

Phe Asp Tyr Ala Thr Ser Glu Phe Gly Cys Lys Leu Asn Leu Thr Thr
        275                 280                 285

Cys Cys Phe Ile Asp Leu Met Cys Phe Leu Gly Leu Ala Arg Glu Pro
290                 295                 300

Lys Arg Val Ser Arg Glu Ala Val Leu Ala Arg Ala Gln Arg Thr Gly
305                 310                 315                 320

Asp Gly Ser His Trp Ser Gly
                325

<210> SEQ ID NO 7
<211> LENGTH: 324
<212> TYPE: PRT
<213> ORGANISM: carp

<400> SEQUENCE: 7

Met Pro Asp Arg Asp Ile Lys Ser Pro Ile Trp His Pro Glu Thr Val
1               5                   10                  15

Glu Asp Val Phe Asp His Thr Tyr Lys Glu Lys Glu Gly Pro Lys Pro
            20                  25                  30

Pro Thr Val Ile Val Trp Arg Asn Val Leu Leu Met Ala Phe Leu His
        35                  40                  45

Thr Gly Ala Leu Tyr Gly Leu Val Leu Phe Pro Ser Ala Ser Val Leu
        50                  55                  60

Thr Trp Ile Trp Phe Leu Ala Cys Phe Val Phe Ser Ala Leu Gly Val

```
                65                  70                  75                  80
Thr Ala Gly Ala His Arg Leu Trp Ser Arg Arg Ser Tyr Lys Ala Ser
                    85                  90                  95

Leu Pro Leu Arg Ile Phe Leu Ala Phe Ala Asn Ser Met Gly Phe Gln
                100                 105                 110

Asn Asp Ile Tyr Glu Trp Ser Arg Asp His Arg Val His His Lys Tyr
                115                 120                 125

Ser Glu Thr Asp Ala Asp Pro His Asn Ala Val Arg Gly Phe Phe
            130                 135                 140

Ser His Ile Gly Trp Leu Leu Val Arg Lys His Pro Asp Val Ile Glu
145                 150                 155                 160

Lys Gly Arg Lys Leu Glu Leu Ser Asp Leu Lys Ala Asp Lys Val Val
                165                 170                 175

Met Phe Gln Arg Arg Phe Tyr Lys Ser Ser Val Leu Leu Met Cys Phe
                180                 185                 190

Phe Val Pro Thr Phe Val Pro Trp Tyr Val Trp Gly Glu Ser Leu Trp
                195                 200                 205

Val Ala Tyr Phe Val Pro Ala Val Leu Arg Tyr Ala Leu Val Leu Asn
210                 215                 220

Ala Thr Trp Leu Val Asn Ser Ala Ala His Met Trp Gly Asn Arg Pro
225                 230                 235                 240

Tyr Asp Ser Ser Ile Asn Pro Arg Glu Asn Arg Phe Val Ala Phe Ser
                245                 250                 255

Ala Ile Gly Glu Gly Phe His Asn Tyr His His Thr Phe Pro Phe Asp
                260                 265                 270

Tyr Ala Thr Ser Glu Phe Gly Cys Lys Leu Asn Leu Thr Thr Cys Phe
                275                 280                 285

Ile Asp Leu Met Cys Phe Leu Gly Leu Ala Arg Glu Pro Lys Arg Val
                290                 295                 300

Ser Arg Glu Ala Ala Leu Ala Arg Ala Gln Arg Thr Gly Asp Gly Ser
305                 310                 315                 320

His Arg Thr Gly

<210> SEQ ID NO 8
<211> LENGTH: 357
<212> TYPE: PRT
<213> ORGANISM: chicken

<400> SEQUENCE: 8

Met Pro Ala His Leu Leu Gln Glu Glu Phe Ser Ser Ala Ser Ser
1                   5                   10                  15

Thr Thr Thr Val Thr Ser Arg Val Thr Lys Asn Gly Asn Val Ile Met
                20                  25                  30

Glu Lys Asp Leu Leu Asn His Asp Asp Val Ala Ala Glu Arg Gly Met
                35                  40                  45

Val Asp Asp Leu Phe Asp Glu Thr Tyr Arg Glu Lys Glu Gly Pro Lys
            50                  55                  60

Pro Pro Leu Arg Tyr Val Trp Arg Asn Ile Ile Leu Met Ser Leu Leu
65                  70                  75                  80

His Leu Gly Ala Ile Ile Gly Leu Thr Leu Ile Pro Ser Ala Lys Ile
                85                  90                  95

Gln Thr Leu Ala Trp Ala Ile Leu Cys Phe Val Leu Ser Ala Leu Gly
                100                 105                 110

Ile Thr Ala Gly Ser His Arg Leu Trp Ser His Arg Ser Tyr Lys Ala
```

```
                115                 120                 125
Thr Leu Pro Leu Arg Ile Phe Leu Thr Ile Ala Asn Ser Met Ala Phe
        130                 135                 140

Gln Asn Asp Ile Tyr Glu Trp Ala Arg Asp His Arg Val His His Lys
145                 150                 155                 160

Phe Ser Glu Thr His Ala Asp Pro His Asn Ala Met Arg Gly Tyr Phe
                165                 170                 175

Phe Ser His Met Ala Trp Leu Leu Val Arg Lys His Pro Asp Val Ile
                180                 185                 190

Glu Lys Gly Gln Lys Leu Asp Leu Ser Asp Leu Lys Ala Asp Lys Val
                195                 200                 205

Val Met Phe Gln Arg Arg Tyr Tyr Lys Pro Ser Val Val Leu Leu Cys
        210                 215                 220

Phe Thr Leu Pro Thr Leu Val Pro Trp Tyr Phe Trp Asp Glu Ser Ile
225                 230                 235                 240

Ile Ile Ser Phe Phe Ile Pro Ala Ile Leu Arg Tyr Thr Leu Gly Leu
                245                 250                 255

Asn Ala Thr Trp Leu Val Asn Ser Ala Ala His Met Phe Gly Asn Arg
                260                 265                 270

Pro Tyr Asp Gln Asn Ile Asn Pro Arg Glu Asn Pro Leu Val Ser Val
                275                 280                 285

Gly Ala Leu Gly Glu Gly Phe His Asn Tyr His His Thr Phe Pro Tyr
        290                 295                 300

Asp Tyr Ser Thr Ser Glu Phe Gly Trp Arg Phe Asn Leu Thr Thr Ala
305                 310                 315                 320

Phe Ile Asp Leu Met Cys Leu Leu Gly Leu Ala Ser Asp Arg Lys Lys
                325                 330                 335

Val Ser Lys Glu Val Ile Leu Ala Arg Lys Met Arg Thr Gly Asp Gly
                340                 345                 350

Ser His Lys Ser Gly
            355

<210> SEQ ID NO 9
<211> LENGTH: 383
<212> TYPE: PRT
<213> ORGANISM: Drosophila melanogaster

<400> SEQUENCE: 9

Met Pro Pro Asn Ala Gln Ala Gly Ala Gln Ser Ile Ser Asp Ser Leu
1               5                   10                  15

Ile Ala Ala Ser Ala Ala Asp Ala Gly Gln Ser Pro Thr Lys
                20                  25                  30

Leu Gln Glu Asp Ser Thr Gly Val Leu Phe Glu Cys Asp Val Glu Thr
            35                  40                  45

Thr Asp Gly Gly Leu Val Lys Asp Ile Thr Val Met Lys Lys Ala Glu
        50                  55                  60

Lys Arg Leu Leu Lys Leu Val Trp Arg Asn Ile Ile Ala Phe Gly Tyr
65                  70                  75                  80

Leu His Leu Ala Ala Leu Tyr Gly Ala Tyr Leu Met Val Thr Ser Ala
                85                  90                  95

Lys Trp Gln Thr Cys Ile Leu Ala Tyr Phe Leu Tyr Val Ile Ser Gly
            100                 105                 110

Leu Gly Ile Thr Ala Gly Ala His Arg Leu Trp Ala His Arg Ser Tyr
            115                 120                 125
```

```
Lys Ala Lys Trp Pro Leu Arg Val Ile Leu Val Ile Phe Asn Thr Ile
130                 135                 140

Ala Phe Gln Asp Ala Ala Tyr His Trp Ala Arg Asp His Arg Val His
145                 150                 155                 160

His Lys Tyr Ser Glu Thr Asp Ala Asp Pro His Asn Ala Thr Arg Gly
                165                 170                 175

Phe Phe Phe Ser His Val Gly Trp Leu Leu Cys Lys Lys His Pro Glu
                180                 185                 190

Val Lys Ala Lys Gly Lys Gly Val Asp Leu Ser Asp Leu Arg Ala Asp
                195                 200                 205

Pro Ile Leu Met Phe Gln Lys Lys Tyr Tyr Met Ile Leu Met Pro Ile
210                 215                 220

Ala Cys Phe Ile Ile Pro Thr Val Val Pro Met Tyr Ala Trp Gly Glu
225                 230                 235                 240

Ser Phe Met Asn Ala Trp Phe Val Ala Thr Met Phe Arg Trp Cys Phe
                245                 250                 255

Ile Leu Asn Val Thr Trp Leu Val Asn Ser Ala Ala His Lys Phe Gly
                260                 265                 270

Gly Arg Pro Tyr Asp Lys Phe Ile Asn Pro Ser Glu Asn Ile Ser Val
                275                 280                 285

Ala Ile Leu Ala Phe Gly Glu Gly Trp His Asn Tyr His His Val Phe
290                 295                 300

Pro Trp Asp Tyr Lys Thr Ala Glu Phe Gly Lys Tyr Ser Leu Asn Phe
305                 310                 315                 320

Thr Thr Ala Phe Ile Asp Phe Phe Ala Lys Ile Gly Trp Ala Tyr Asp
                325                 330                 335

Leu Lys Thr Val Ser Thr Asp Ile Ile Lys Lys Arg Val Lys Arg Thr
                340                 345                 350

Gly Asp Gly Thr His Ala Thr Trp Gly Trp Gly Asp Val Asp Gln Pro
                355                 360                 365

Lys Glu Glu Ile Glu Asp Ala Val Ile Thr His Lys Lys Ser Glu
370                 375                 380

<210> SEQ ID NO 10
<211> LENGTH: 280
<212> TYPE: PRT
<213> ORGANISM: Caenorhabditis elegans

<400> SEQUENCE: 10

Met Thr Val Lys Thr Arg Ser Asn Ile Ala Lys Lys Ile Glu Lys Asp
1               5                   10                  15

Gly Gly Pro Glu Thr Gln Tyr Leu Ala Val Asp Pro Asn Glu Ile Ile
                20                  25                  30

Gln Leu Gln Glu Glu Ser Lys Lys Ile Pro Tyr Lys Met Glu Ile Val
                35                  40                  45

Trp Arg Asn Val Ala Leu Phe Ala Ala Leu His Phe Ala Ala Ala Ile
            50                  55                  60

Gly Leu Tyr Gln Leu Ile Phe Glu Ala Lys Trp Gln Thr Val Ile Phe
65                  70                  75                  80

Thr Phe Leu Leu Tyr Val Phe Gly Gly Phe Gly Ile Thr Ala Gly Ala
                85                  90                  95

His Arg Leu Trp Ser His Lys Ser Tyr Lys Ala Thr Thr Pro Met Arg
                100                 105                 110

Ile Phe Leu Met Ile Leu Asn Asn Ile Ala Leu Gln Asn Asp Val Ile
                115                 120                 125
```

```
Glu Trp Ala Arg Asp His Arg Cys His His Lys Trp Thr Asp Thr Asp
    130                 135                 140

Ala Asp Pro His Asn Thr Thr Arg Gly Phe Phe Ala His Met Gly
145                 150                 155                 160

Trp Leu Leu Val Arg Lys His Pro Gln Val Lys Glu Gln Gly Ala Lys
                165                 170                 175

Leu Asp Met Ser Asp Leu Leu Ser Asp Pro Val Leu Val Phe Gln Arg
            180                 185                 190

Lys His Tyr Phe Pro Leu Val Ile Leu Cys Cys Phe Ile Leu Pro Thr
        195                 200                 205

Ile Ile Pro Val Tyr Phe Trp Lys Glu Thr Ala Phe Ile Ala Phe Tyr
    210                 215                 220

Thr Ala Gly Thr Phe Arg Tyr Cys Phe Thr Leu His Ala Thr Trp Cys
225                 230                 235                 240

Ile Asn Ser Ala Ala His Tyr Phe Gly Trp Lys Pro Tyr Asp Ser Ser
                245                 250                 255

Ile Thr Pro Val Glu Asn Val Phe Thr Thr Ile Ala Ala Val Gly Glu
            260                 265                 270

Gly Gly His Asn Lys Ser Ile Met
        275                 280

<210> SEQ ID NO 11
<211> LENGTH: 288
<212> TYPE: PRT
<213> ORGANISM: mouse

<400> SEQUENCE: 11

Met Pro Ala His Met Leu Gln Glu Ile Ser Ser Ser Tyr Thr Thr Thr
1               5                   10                  15

Thr Thr Ile Thr Ala Pro Pro Ser Gly Asn Glu Arg Glu Lys Val Lys
            20                  25                  30

Thr Val Pro Leu His Leu Glu Glu Asp Ile Arg Pro Glu Met Lys Glu
        35                  40                  45

Asp Ile His Asp Pro Thr Tyr Gln Asp Glu Gly Pro Pro Lys
    50                  55                  60

Leu Glu Tyr Val Trp Ala Asn Ile Ile Leu Met Val Leu Leu His Leu
65                  70                  75                  80

Gly Gly Leu Tyr Gly Ile Ile Leu Val Pro Ser Cys Lys Leu Tyr Thr
                85                  90                  95

Cys Leu Phe Gly Ile Phe Tyr Tyr Met Thr Ser Ala Leu Gly Ile Thr
            100                 105                 110

Ala Gly Ala His Arg Leu Trp Ser His Arg Thr Tyr Lys Ala Arg Leu
        115                 120                 125

Pro Leu Arg Ile Phe Leu Ile Ile Ala Asn Thr Met Ala Phe Gln Asn
    130                 135                 140

Asp Val Tyr Glu Trp Ala Arg Asp His Arg Ala His His Lys Phe Ser
145                 150                 155                 160

Glu Thr His Ala Asp Pro His Asn Ser Arg Arg Gly Phe Phe Phe Ser
                165                 170                 175

His Val Gly Trp Leu Leu Val Ala Lys His Pro Ala Val Lys Glu Lys
            180                 185                 190

Gly Gly Lys Leu Asp Met Ser Asp Leu Lys Ala Glu Lys Leu Val Met
        195                 200                 205

Phe Gln Arg Arg Tyr Tyr Lys Pro Gly Leu Leu Leu Met Cys Phe Ile
```

-continued

```
            210                 215                 220
Leu Pro Thr Leu Val Pro Trp Tyr Cys Trp Gly Glu Thr Phe Val Asn
225                 230                 235                 240

Ser Leu Phe Val Ser Thr Phe Leu Arg Tyr Thr Leu Val Leu Asn Ala
                245                 250                 255

Thr Trp Leu Val Asn Ser Ala Ala His Leu Tyr Gly Tyr Arg Pro Tyr
                260                 265                 270

Asp Lys Ile Gln Ser Arg Glu Asn Ile Leu Val Ser Leu Gly Ala Val
                275                 280                 285

<210> SEQ ID NO 12
<211> LENGTH: 358
<212> TYPE: PRT
<213> ORGANISM: mouse

<400> SEQUENCE: 12

Met Pro Gly His Leu Leu Gln Glu Glu Met Thr Pro Ser Tyr Thr Thr
1               5                   10                  15

Thr Thr Thr Ile Thr Ala Pro Pro Ser Gly Ser Leu Gln Asn Gly Arg
                20                  25                  30

Glu Lys Val Lys Thr Val Pro Leu Tyr Leu Glu Glu Asp Ile Arg Pro
            35                  40                  45

Glu Met Lys Glu Asp Ile Tyr Asp Pro Thr Tyr Gln Asp Glu Glu Gly
50                  55                  60

Pro Pro Pro Lys Leu Glu Tyr Val Trp Ala Asn Ile Ile Leu Met Ala
65                  70                  75                  80

Leu Leu His Val Gly Ala Leu Tyr Gly Ile Thr Leu Val Pro Ser Cys
                85                  90                  95

Lys Leu Tyr Thr Cys Leu Phe Ala Phe Val Tyr Val Ile Ser Ile
                100                 105                 110

Glu Gly Ile Gly Ala Gly Val His Arg Leu Trp Ser His Arg Thr Tyr
            115                 120                 125

Lys Ala Arg Leu Pro Leu Arg Ile Phe Leu Ile Ile Ala Asn Thr Met
130                 135                 140

Ala Phe Gln Asn Asp Val Tyr Glu Trp Ala Arg Asp His Arg Ala His
145                 150                 155                 160

His Lys Phe Ser Glu Thr His Ala Asp Pro His Asn Ser Arg Arg Gly
                165                 170                 175

Phe Phe Phe Ser His Val Gly Trp Leu Leu Val Arg Lys His Pro Ala
                180                 185                 190

Val Lys Glu Lys Gly Gly Lys Leu Asp Met Ser Asp Leu Lys Ala Glu
            195                 200                 205

Lys Leu Val Met Phe Gln Arg Arg Tyr Tyr Lys Pro Gly Ile Leu Leu
210                 215                 220

Met Cys Phe Ile Leu Pro Thr Leu Val Trp Tyr Cys Trp Gly Glu Thr
225                 230                 235                 240

Phe Leu Asn Ser Phe Tyr Val Ala Thr Leu Leu Arg Tyr Ala Val Val
                245                 250                 255

Leu Asn Ala Thr Trp Leu Val Asn Ser Ala Ala His Leu Tyr Gly Tyr
                260                 265                 270

Arg Pro Tyr Asp Lys Asn Ile Asp Pro Arg Gln Asn Ala Leu Val Ser
            275                 280                 285

Leu Gly Ser Met Gly Glu Gly Phe His Asn Tyr His His Ala Phe Pro
        290                 295                 300
```

```
-continued

Tyr Asp Tyr Ser Ala Ser Glu Tyr Arg Trp His Ile Asn Phe Thr Thr
305                 310                 315                 320

Phe Phe Ile Asp Cys Met Ala Ala Leu Gly Leu Ala Tyr Asp Arg Lys
            325                 330                 335

Arg Val Ser Lys Ala Thr Val Leu Ala Arg Ile Lys Arg Thr Gly Asp
            340                 345                 350

Gly Ser His Lys Ser Gly
        355

<210> SEQ ID NO 13
<211> LENGTH: 24
<212> TYPE: DNA
<213> ORGANISM: artificial
<220> FEATURE:
<223> OTHER INFORMATION: PCR Primer

<400> SEQUENCE: 13
caccatgcca ggcccggcca ccga                                  24

<210> SEQ ID NO 14
<211> LENGTH: 18
<212> TYPE: DNA
<213> ORGANISM: Artificial
<220> FEATURE:
<223> OTHER INFORMATION: PCR Primer

<400> SEQUENCE: 14
agcactgctg tccagtcc                                         18
```